(12) United States Patent
Boulos et al.

(10) Patent No.: US 10,793,495 B2
(45) Date of Patent: Oct. 6, 2020

(54) SYNTHESIS OF POLYARYL SUBSTITUTED ARYL COMPOUNDS

(71) Applicant: Boulos & Cooper Pharmaceuticals Pty Ltd, Balcatta, Western Australia (AU)

(72) Inventors: Ramiz Boulos, Banksia Grove (AU); John Feutrill, Rosana (AU)

(73) Assignee: Boulos & Cooper Pharmaceuticals Pty Ltd, Balcatta, WA (AU)

( * ) Notice: Subject to any disclaimer, the term of this patent is extended or adjusted under 35 U.S.C. 154(b) by 0 days.

(21) Appl. No.: 15/748,514

(22) PCT Filed: Aug. 8, 2016

(86) PCT No.: PCT/AU2016/095003
§ 371 (c)(1),
(2) Date: Jan. 29, 2018

(87) PCT Pub. No.: WO2017/027933
PCT Pub. Date: Feb. 23, 2017

(65) Prior Publication Data
US 2018/0215687 A1   Aug. 2, 2018

(30) Foreign Application Priority Data

Aug. 14, 2015 (AU) ................................ 2015903284

(51) Int. Cl.
| | | |
|---|---|---|
| C07C 69/76 | (2006.01) | |
| C07C 15/52 | (2006.01) | |
| C07C 1/32 | (2006.01) | |
| C07C 67/343 | (2006.01) | |
| A61P 31/04 | (2006.01) | |
| C07C 2/68 | (2006.01) | |
| C07C 2/70 | (2006.01) | |
| C07C 5/09 | (2006.01) | |
| C07C 7/10 | (2006.01) | |
| C07C 15/46 | (2006.01) | |
| C07C 25/28 | (2006.01) | |

(52) U.S. Cl.
CPC .............. *C07C 15/52* (2013.01); *A61P 31/04* (2018.01); *C07C 1/321* (2013.01); *C07C 2/68* (2013.01); *C07C 2/70* (2013.01); *C07C 5/09* (2013.01); *C07C 7/10* (2013.01); *C07C 15/46* (2013.01); *C07C 67/343* (2013.01); *C07C 25/28* (2013.01); *C07C 2523/44* (2013.01); *C07C 2531/24* (2013.01)

(58) Field of Classification Search
CPC ..................................................... C07C 69/76
USPC ....................................................... 560/76
See application file for complete search history.

(56) References Cited

FOREIGN PATENT DOCUMENTS

| CN | 102746124 A | 10/2012 |
| JP | 2010-146864 A | 7/2010 |
| WO | WO-2004/058759 A1 | 7/2004 |
| WO | WO-2006/028451 A1 | 3/2006 |
| WO | WO-2011/075766 A1 | 6/2011 |
| WO | WO 17/027933 * | 2/2017 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Alacid et al., General reaction conditions for the palladium-catalyzed vinylation of aryl chlorides with potassium alkenyltrifluoroborates, J. Org. Chem., 74(21):8191-5 (2009).
Alacid et al., Palladium-catalyzed cross-coupling reactions of potassium alkenyltrifluoroborates with organic halides in aqueous media, J. Org. chem., 74(6):2321-7 (2009).
Hayashi et al., Triethylsilane-indium(III) chloride system as a radical reagent, Org. Lett., 6(26):4981-3 (2004).
International Application No. PCT/AU2016/095003, International Preliminary Report on Patentability, dated Feb. 20, 2018.
International Application No. PCT/AU2016/095003, International Search Report and Written Opinion, dated Nov. 29, 2016.
Joucla et al., Efficient heterogeneous vinylation of aryl halides using potassium vinyltrifluoroborate, Tetrahedron Lett., 49(32):4738-41 (2008).
Joucla et al., Heterogeneously Pd/C catalysed procedure for the vinylation of aryl bromides, 360(2):145-53 (2009).
Joucla et al., One-Pot Suzuki/Heck Sequence for the Synthesis of (E)-Stilbenes Featuring a Recyclable Silica-Supported Palladium Catalyst via a Multi-Component Reaction in 1,3-Propanediol , Adv. Synthesis & Catalysis, 352(11-12):1993-2001 (2010).
Lengkeek et al., The synthesis of fluorescent DNA intercalator precursors through efficient multiple heck reactions, Aust. J. Chem., 64(3):316-23 (2011).
Li et al., Highly chemo- and stereoselective palladium-catalyzed transfer semihydrogenation of internal alkynes affording cis-alkenes, J. Org. Chem., 75(9):2966-70 (2010).
Molander et al., Development of the suzuki-miyaura cross-coupling reaction: use of air-stable potassium alkynyltrifluoroborates in aryl alkynylations, J. Org. Chem., 67(24):8416-23 (2002).
Molander et al., Suzuki-Miyaura cross-coupling reactions of potassium alkenyltrifluoroborates, J. Org. Chem., 67(24):8424-9 (2002).
Molander et al., Suzuki-Miyaura cross-coupling reactions of potassium vinyltrifluoroborate with aryl and heteroaryl electrophiles, J. Org. Chem., 71(26):9681-6 (2006).
Pawluc et al., New one-pot synthesis of (E)-beta-aryl vinyl halides from styrenes, Org. Lett., 11(15):3390-3 (2009).
Schabel et al., A mild chemoselective Ru-catalyzed reduction of alkynes, ketones, and nitro compounds, Org. Lett., 15(11):2858-61 (2013).

(Continued)

*Primary Examiner* — Douglas M Willis
(74) *Attorney, Agent, or Firm* — Marshall, Gerstein & Borun LLP

(57) ABSTRACT

A method for the synthesis of a aryl compound of Formula (1).

$$U\text{-}(\text{-}T\text{-}W\text{-}R_1)_n \quad (1)$$

21 Claims, 7 Drawing Sheets

(56) References Cited

OTHER PUBLICATIONS

Severin et al., One-pot procedure for the synthesis of unsymmetrical diarylalkynes, J. Org. Chem., 75(10):3518-21 (2010).

Shen et al., Facile regio- and stereoselective hydrometalation of alkynes with a combination of carboxylic acids and group 10 transition metal complexes: selective hydrogenation of alkynes with formic acid, J. Am. Chem. Soc., 133(42):17037-44 (2011).

Tang et al., Efficient Palladium-Catalyzed Cross-Coupling Reaction of Alkynyl Halides with Organoboronic Acids under Aerobic Conditions, Synthesis, 44:541-6 (2012).

Wang et al., Palladium-catalyzed cross-coupling of aryl electrophiles with dimethylalkynylaluminum reagents, Org. Lett., 6(20):3481-4 (2004).

Whittaker et al., Monophasic catalytic system for the selective semireduction of alkynes, Org. Lett., 15(5):1112-5 (2013).

Beletskaya et al., The Heck Reaction as a Sharpening Stone of Palladium Catalysis, *Chem. Rev.* 100:3009-66 (2000).

Molander et al., Cross-Coupling Reactions of Organotrifluoroborate Salts, Organic Reactions, John Wiley & Sons, Inc. (2013).

Meijere et al., Metal-Catalyzed Cross-Coupling Reactions, 2nd ed., Wiley-VCH (2004).

\* cited by examiner

Neat Pet.Ether

S:1

M:S+R

R: reaction mixture

Rf = 0.7

SYNTHESIS OF POLYARYL SUBSTITUTED ARYL COMPOUNDS

TECHNICAL FIELD

The present invention provides methods for the synthesis of aryl compounds, and the use thereof as pharmaceuticals.

BACKGROUND OF THE INVENTION

Compounds with antimicrobial properties have attracted great interest in recent times as a result of an increase in the prevalence of infections caused by Gram-positive bacteria, resulting in serious or fatal diseases. Furthermore, the regular use of broad spectrum antibiotic formulas has led to the increased occurrence of bacterial strains resistant to some antimicrobial formulations.

Novel antimicrobial compounds have the potential to be highly effective against these types of treatment-resistant bacteria. The pathogens, having not previously been exposed to the antimicrobial formulation, may have little to no resistance to the treatment.

International patent application WO 2011/075766 describes a series of novel aryl compounds and their use as antimicrobials to treat bacterial infections or diseases. The chemical synthesis of a therapeutic drug has a direct effect on its cost, dosing regimens and popularity. Drugs with complicated or expensive chemical synthesis will find it challenging to reach the market, notwithstanding their efficacy. Further, syntheses amenable to application at commercial scales are highly advantageous. The development of an efficient and large-scale synthesis of a therapeutic drug is critical for its drug developmental pathway, and highly commercially advantageous.

The above discussion of the background art is intended to facilitate an understanding of the present invention only. The discussion is not an acknowledgement or admission that any of the material referred to is or was part of the common general knowledge as at the priority date of the application.

BRIEF SUMMARY OF THE INVENTION

The invention provides a method for the synthesis of a compound of Formula (1);

U-(-T-W—R$_1$)$_n$    Formula (1)

the method comprising the step of:
reacting a compound of Formula (2);

U-(-X)$_n$    Formula (2)

with a compound of Formula (3);

V—Y    Formula (3)

under a first set of reaction conditions, to produce a compound of Formula (4):

U-(-V)$_n$    Formula (4)

then reacting the compound of Formula (4) with one or more reagents under a second set of reaction conditions to produce the compound of Formula (1);
where;
n is 1-6;
U is a benzene or pyridine;
T is -, = or ≡;
V is = or ≡;
W is a benzene or pyridine;
Y is —B$^{K-}$G$_I$M$^{J+}$;
G is a halogen;
M is any Group (I) or Group (II) metal;
K is 1 or 2;
I is 3 or 4;
J is 1 or 2;
X is a halogen;
each R$_1$ may be independently selected from any one or more of i-xxxiii:
 i. H;
 ii. C$_{1-8}$ alkyl;
 iii. C$_{1-8}$ heteroalkyl;
 iv. carboxylic acids and related derivatives independently selected from:
  a) carboxylic acid,

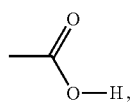

b) alkyl carboxylic acid,

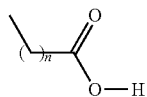

where n=0-3;
  c) thiocarboxylic acid,

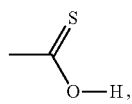

d) alkyl thiocarboxylic acid,

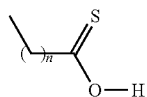

where n=0-3;
  e) esters,

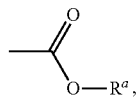

f) alkyl esters,

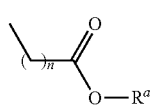

where n=1-8;

g) thioesters, $$\underset{O-R^a}{\overset{S}{\parallel}}$$

h) alkyl thioesters, $$\underset{O-R^a}{(\ )_n\overset{S}{\parallel}}$$

where n=1-8 i) dithioesters, $$\underset{S-R^a}{\overset{S}{\parallel}}$$

j) alkyl dithioesters, $$\underset{S-R^a}{(\ )_n\overset{S}{\parallel}}$$

where n=1-8 v. amide derivatives of carboxylic acids independently selected from:

k) amides, $$\underset{\underset{R^b}{N-R^a}}{\overset{O}{\parallel}}$$

l) thioamides, $$\underset{\underset{R^b}{N-R^a}}{\overset{S}{\parallel}}$$

vi. aldehydes, ketones and their derivatives independently selected from:

m) aldehyde, $$\overset{O}{\underset{H}{\parallel}}$$

n) thial, $$\overset{S}{\underset{H}{\parallel}}$$

o) ketones, $$\underset{R^a}{\overset{O}{\parallel}}$$

p) thioketones, $$\underset{R^a}{\overset{S}{\parallel}}$$

q) acetals, $$\underset{O-R^b}{\overset{O-R^a}{|}} \quad \overset{R^a}{\underset{O\ R^b}{\diamond}} \quad \overset{O}{\underset{O}{\diamond}})_n,$$

where n=1-3 r) dithioacetals, $$\underset{S-R^b}{\overset{S-R^a}{|}} \quad \overset{R^a}{\underset{S\ R^b}{\diamond}} \quad \overset{S}{\underset{S}{\diamond}})_n,$$

where n=1-3 vii. amines, alkyl amines and their derivatives independently selected from:

s) amines, $$-N\underset{R^b}{\overset{R^a}{\diagup}}$$

t) amides, $$-N\underset{\underset{O}{\overset{\parallel}{R^b}}}{\overset{R^a}{\diagup}}$$

u) thioamides,

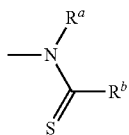

v) ammonium salts,

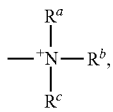

w) alkyl amines,

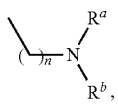

where n=1-8
x) alkyl amides,

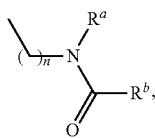

where n=1-8
y) alkyl thioamides,

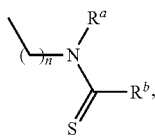

where n=1-8
z) alkyl ammonium salts,

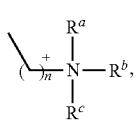

where n=1-8,
aa) imines,

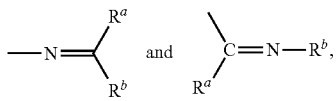

bb) guanidines,

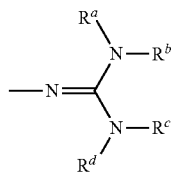

cc) amidines,

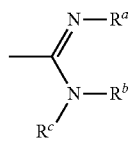

viii. nitrile (cyano), —C≡N,
ix. isonitrile, —N⁺≡C⁻,
x. cyanate, —O—C≡N,
xi. isocyanate, —N=C=O,
xii. thiocyanate, —S—C≡N,
xiii. isothiocyanate, —N=C=S,
xiv. azo, —N=NH,
xv. nitro,

xvi. nitrite, —O—N=O,
xvii. nitriso, —N=O,
xviii. N-terminal peptide sequences,

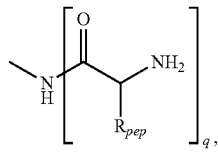

where q=1-3 and $R_{pep}$ is any group resulting in the formation of an amino acid,
xix. C-terminal peptide sequences,

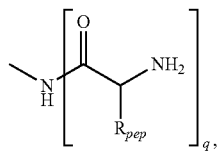

where q=1-3 and $R_{pep}$ is any group resulting in the formation of an amino acid,
xx. phosphorus based substituents, where the phosphorus atom is in either the 3⁺ or 5⁺ oxidation state, independently selected from:

dd) alkyl phosphines,
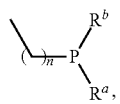
where n=1-8
ee) alkyl phosphonium salts,
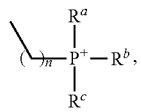
where n=0-8
ff) phosphines,
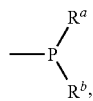
gg) phosphine oxides,
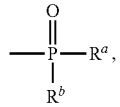
hh) phosphites,
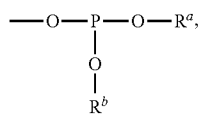
ii) phosphates,
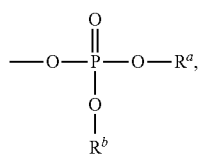
jj) phosphinites,
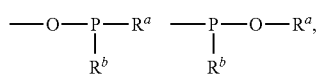
kk) phosphinates,
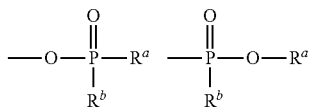
ll) phosphinites,
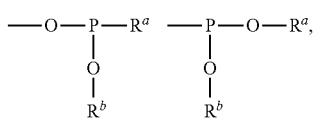
mm) phosphonates,
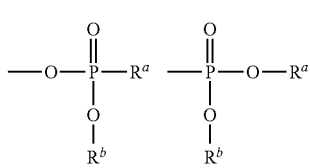
xxi. sulfur based substituents,
nn) sulfate,
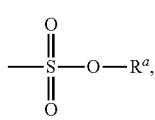
oo) sulfone,
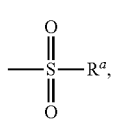
pp) sulfoxide,
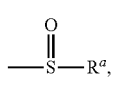
qq) sulfinic acids,
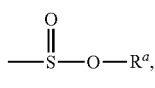
rr) sulfimines,
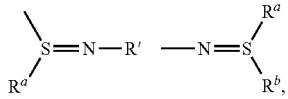

ss) sulfon amides,
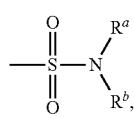
tt) triflates,
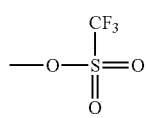
xxii. boron based substituents,
   uu) boronic acid,
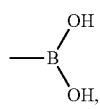
vv) boronic esters,
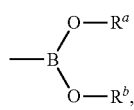
xxiii. semicarbazones,
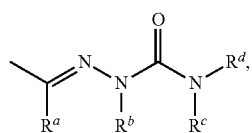
xxiv. thiosemicarbazones,
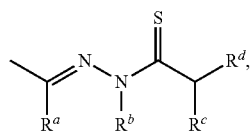
xxv. cyanimide,
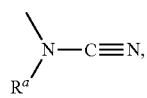
xxvi. hydrazone,
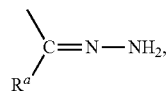
xxvii. oxime,
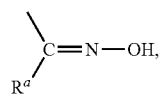
xxviii. nitroamine,
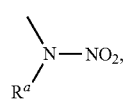
xxix. nitronate,
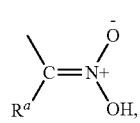
xxx. nitrone,
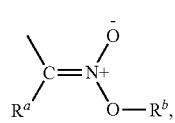
xxxi. carbonates,
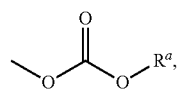
xxxii. carbamates,
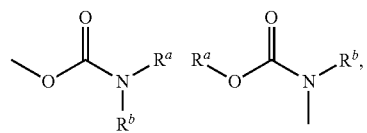
xxxiii. dithiocarbamates,
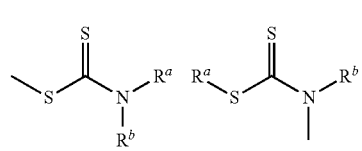

where $R_a$, $R_b$, $R_c$ and $R_d$ in i-xxxiii are independently selected from hydrogen or alkyl ($C_{1-4}$).

The invention also provides a method for the synthesis of a compound of Formula (1);

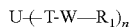  Formula (1)

the method comprising the step of:
reacting a compound of Formula (2);

  Formula (2)

with a compound of Formula (3);

  Formula (3)

under a first set of reaction conditions, to produce a compound of Formula (4):

  Formula (4)

then reacting the compound of Formula (4) with one or more reagents under a second set of reaction conditions to produce the compound of Formula (1);
where;
n is 1-6;
U is a benzene or pyridine;
T is -, = or ≡;
V is = or ≡;
W is a benzene or pyridine;
Y is $-B^K\text{-}G_IM^{J+}$;
G is a halogen;
M is any Group (I) or Group (II) metal;
K is 1 or 2;
I is 3 or 4;
J is 1 or 2;
X is a halogen;
each $R_1$ may be independently selected from any one or more of i-xxxiii:
  i. H;
  ii. $C_{1-8}$ alkyl;
  iii. $C_{1-8}$ heteroalkyl;
  iv. carboxylic acids and related derivatives independently selected from:
    a) carboxylic acid,

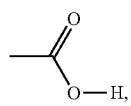

b) alkyl carboxylic acid,

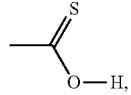

where n=0-3;
  c) thiocarboxylic acid, d) alkyl thiocarboxylic acid,

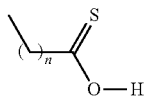

where n=0-3;
  e) esters,

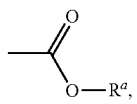

f) alkyl esters,

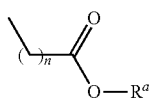

where n=0-3;
  g) thioesters,

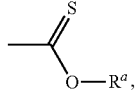

h) alkyl thioesters,

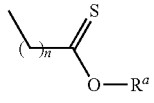

where n=0-3
  i) dithioesters,

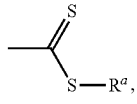

j) alkyl dithioesters,

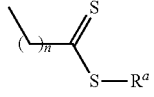

where n=0-3
  v. amide derivatives of carboxylic acids independently selected from:

k) amides,
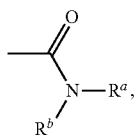
l) thioamides,
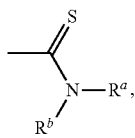
vi. aldehydes, ketones and their derivatives independently selected from:
m) aldehyde,
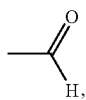
n) thial,
o) ketones,
p) thioketones,
q) acetals,
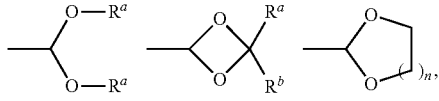
where n=1-3
r) dithioacetals,
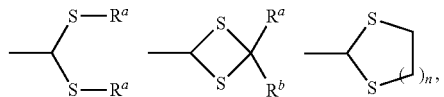
where n=1-3
vii. amines, alkyl amines and their derivatives independently selected from:
s) amines,
t) amides,
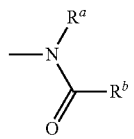
u) thioamides,
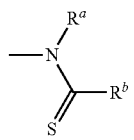
v) ammonium salts,
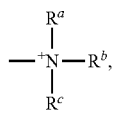
w) alkyl amines,
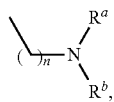
where n=1-3
x) alkyl amides,
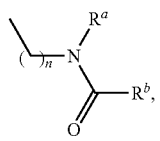
where n=1-3 y) alkyl thioamides,

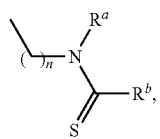

where n=1-3 z) alkyl ammonium salts,

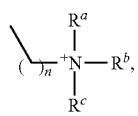

where n=1-3, aa) imines,

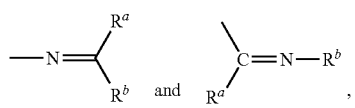

bb) guanidines,

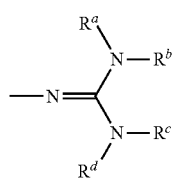

cc) amidines,

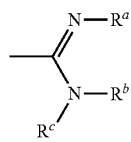

viii. nitrile (cyano), —C≡N,
ix. isonitrile, —N⁺≡C⁻,
x. cyanate, —O—C≡N,
xi. isocyanate, —N=C=O,
xii. thiocyanate, —S—C≡N,
xiii. isothiocyanate, —N=C=S,
xiv. azo, —N=NH,
xv. nitro,

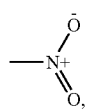

xvi. nitrite, —O—N=O, xvii. nitriso, —N=O,
xviii. N-terminal peptide sequences,

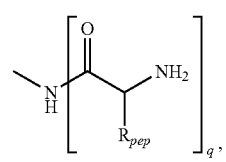

where q=1-3 and $R_{pep}$ is any group resulting in the formation of an amino acid, xix. C-terminal peptide sequences,

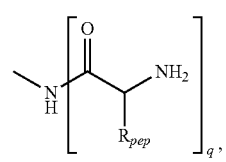

where q=1-3 and $R_{pep}$ is any group resulting in the formation of an amino acid, xx. phosphorus based substituents, where the phosphorus atom is in either the $3^+$ or $5^+$ oxidation state, independently selected from:

dd) phosphines,

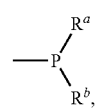

ee) phosphine oxides,

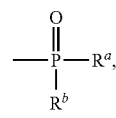

ff) phosphites,

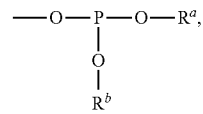

gg) phosphates,

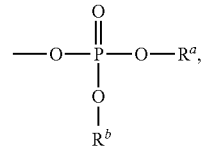

hh) phosphinites,

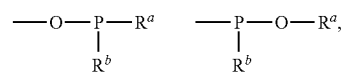

ii) phosphinates,
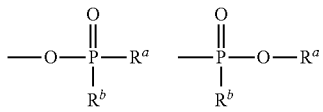
jj) phosphinites,
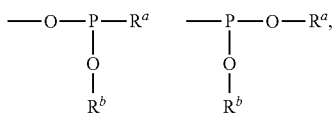
kk) phosphonates,
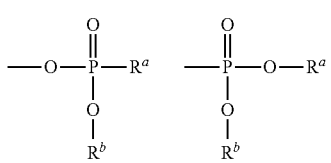
xxi. sulfur based substituents,
ll) sulfate,
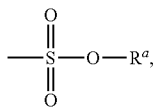
mm) sulfone,
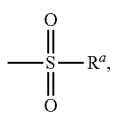
nn) sulfoxide,
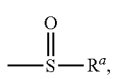
oo) sulfinic acids,
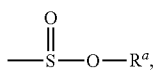
pp) sulfimines,
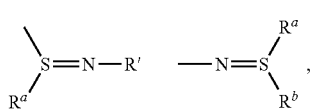
qq) sulfon amides,
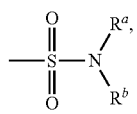
rr) triflates,
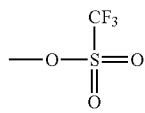
xxii. boron based substituents,
ss) boronic acid,
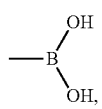
tt) boronic esters,
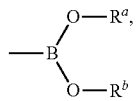
xxiii. semicarbazones,
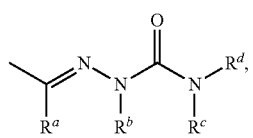
xxiv. thiosemicarbazones,
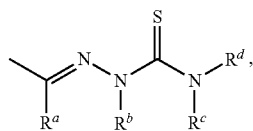
xxv. cyanimide,
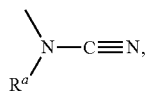

xxvi. hydrazone,

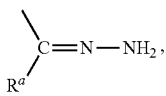

xxvii. oxime,

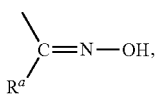

xxviii. nitroamine,

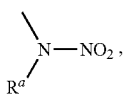

xxix. nitronate,

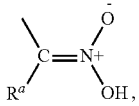

xxx. nitrone,

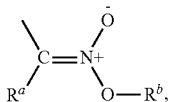

xxxi. carbonates,

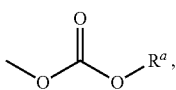

xxxii. carbamates,

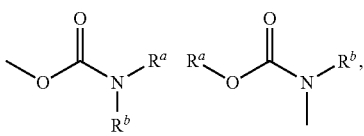

xxxiii. dithiocarbamates,

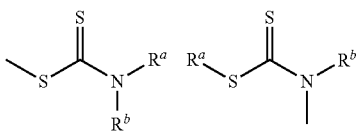

where $R_a$, $R_b$, $R_c$ and $R_d$ in i-xxxiii are independently selected from hydrogen or alkyl ($C_{1-4}$).

DETAILED DESCRIPTION OF THE INVENTION

Figure 1:
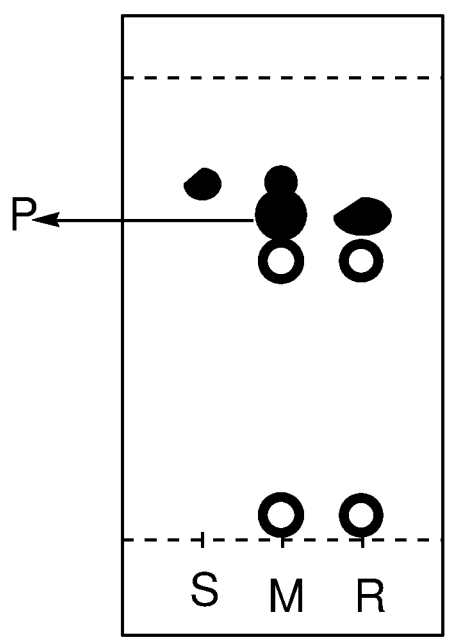
FIG. 1 illustrates column chromatography of compound 5 as described in the Examples.

International patent application WO 2011/075766 describes the synthesis of a series of novel aryl compounds and their use as antimicrobials to treat bacterial infections or diseases. The method of the present invention provides an alternate synthetic method for the novel aryl compounds of WO 2011/075766 to that disclosed in WO 2011/075766. However, method of the present invention has application beyond the scope of the compounds disclosed in WO 2011/075766, and the application of the present invention should not be understood to be constrained to those compounds.

The example syntheses for the compounds of WO 2011/075766 utilises the palladium-catalysed arylation of an alkene. This synthetic approach was first reported by Mizoroki and Heck in the early 1970s and rapidly gained popularity. The classical reaction has since become known as the Heck reaction.

The standard conditions for the Heck reaction [See, for example, Lengkeek, N. A. et al. The Synthesis of Fluorescent DNA Intercalator Precursors through Efficient Multiple Heck Reactions. *Aust J Chem* 64, 316-323, doi:Doi 10.1071/Ch10374 (2011)] are as follows. To a flame-dried schlenk flask was added the halobenzene (1 equiv.), $Pd_2(dba)_3CHCl_3$ (2-15 mol-%) and $[(t-Bu)_3PH]BF_4$ (10-60 mol-%) which were subsequently dried under vacuum for 15 min before being dissolved in dry tetrahydrofuran (THF). N-Methyldicyclohexylamine (4 equiv.) and either ethyl 4-vinylbenzoate or methyl 2-(4-vinylphenyl)acetate (3.3 equiv.) were added via syringe and the reaction monitored by thin-layer chromatography (neat $CH_2Cl_2$). Upon completion of the reaction the residual THF was removed under vacuum, the crude material redissolved in $CH_2Cl_2$ and filtered to remove any insoluble material before being absorbed onto fine silica and eluting with 0:100 to 2:98 $MeOH/CH_2Cl_2$.

However, while effective, the Heck methodology described in WO 2011/075766 presents challenges at commercial scales, due to its high sensitivity to water.

In one form of the invention, the invention provides a method for the synthesis of a compound of Formula (1);

  Formula (1)

the method comprising the step of:
reacting a compound of Formula (2);

U—(X)$_n$  Formula (2)

with a compound of Formula (3);

V—Y  Formula (3)

under a first set of reaction conditions, to produce a compound of Formula (4):

$$U\text{---}(V)_n \qquad \text{Formula (4)}$$

then reacting the compound of Formula (4) with one or more reagents under a second set of reaction conditions to produce the compound of Formula (1);

where;

n is 1-6;

U is a benzene or pyridine;

T is -, = or ≡;

V is = or ≡;

W is a benzene or pyridine;

Y is —$B^{K-}G_I M^{J+}$;

G is a halogen;

M is any Group (I) or Group (II) metal;

K is 1 or 2;

I is 3 or 4;

J is 1 or 2;

X is a halogen;

each $R_1$ may be independently selected from any one or more of i-xxxiii:

i. H;
 ii. $C_{1-8}$ alkyl;
 iii. $C_{1-8}$ heteroalkyl;
 iv. carboxylic acids and related derivatives independently selected from:
  a) carboxylic acid,

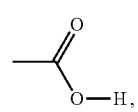

b) alkyl carboxylic acid,

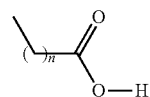

where n=1-8;
  c) thiocarboxylic acid,

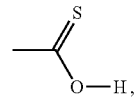

d) alkyl thiocarboxylic acid,

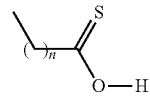

where n=1-8;

e) esters,

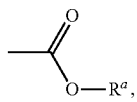

f) alkyl esters,

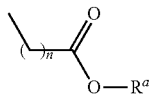

where n=1-8;
  g) thioesters,

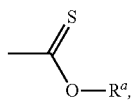

h) alkyl thioesters,

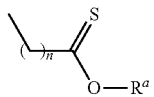

where n=1-8
  i) dithioesters,

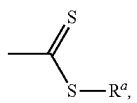

j) alkyl dithioesters,

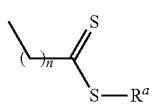

where n=1-8
 v. amide derivatives of carboxylic acids independently selected from:
  k) amides,

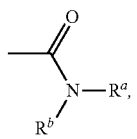

l) thioamides,

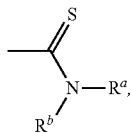

vi. aldehydes, ketones and their derivatives independently selected from:

m) aldehyde,

n) thial,

o) ketones,

p) thioketones,

q) acetals,

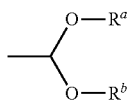

where n=1-3 r) dithioacetals,

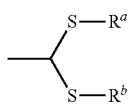

where n=1-3 vii. amines, alkyl amines and their derivatives independently selected from:

s) amines,

t) amides,

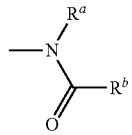

u) thioamides,

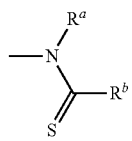

v) ammonium salts,

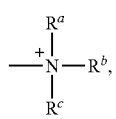

w) alkyl amines,

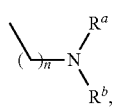

where n=1-8 x) alkyl amides,

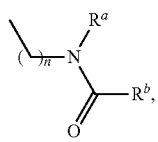

where n=1-8 y) alkyl thioamides,

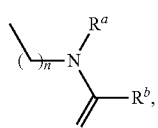

where n=1-8 z) alkyl ammonium salts,

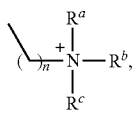

where n=1-8,
aa) imines,

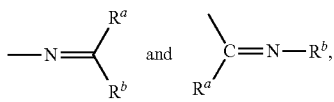

bb) guanidines,

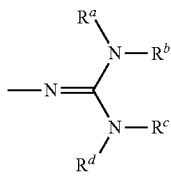

cc) amidines,

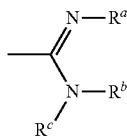

viii. nitrile (cyano), —C≡N,
ix. isonitrile, —N⁺≡C⁻,
x. cyanate, —O—C≡N,
xi. isocyanate, —N=C=O,
xii. thiocyanate, —S—C≡N,
xiii. isothiocyanate, —N=C=S,
xiv. azo, —N=NH,
xv. nitro,

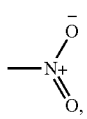

xvi. nitrite, —O—N=O,
xvii. nitriso, —N=O,
xviii. N-terminal peptide sequences,

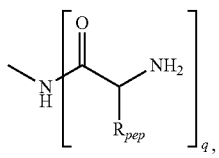

where q=1-3 and $R_{pep}$ is any group resulting in the formation of an amino acid, xix. C-terminal peptide sequences,

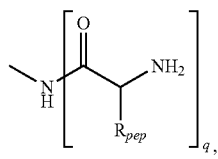

where q=1-3 and $R_{pep}$ is any group resulting in the formation of an amino acid, xx. phosphorus based substituents, where the phosphorus atom is in either the 3⁺ or 5⁺ oxidation state, independently selected from:

dd) alkyl phosphines,

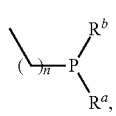

where n=1-8
ee) alkyl phosphonium salts,

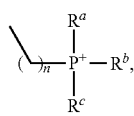

where n=0-8
ff) phosphines,

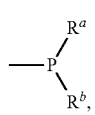

gg) phosphine oxides,

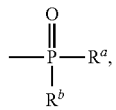

hh) phosphites,

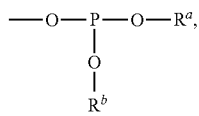

ii) phosphates,
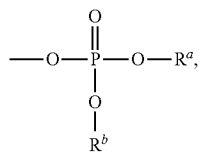
jj) phosphinites,
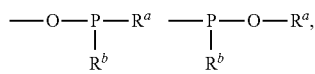
kk) phosphinates,
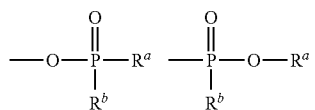
ll) phosphinites,
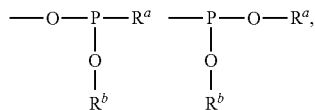
mm) phosphonates,
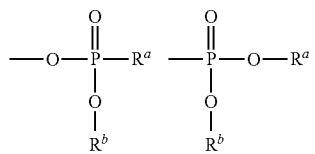
xxi. sulfur based substituents,
  nn) sulfate,
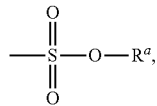
oo) sulfone,
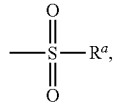
pp) sulfoxide,
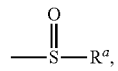
qq) sulfinic acids,
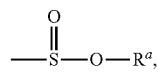
rr) sulfimines,
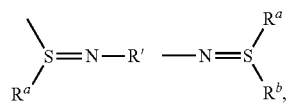
ss) sulfon amides,
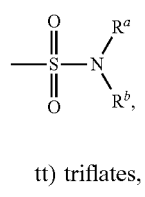
tt) triflates,
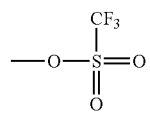
xxii. boron based substituents,
  uu) boronic acid,
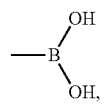
vv) boronic esters,
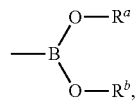
xxiii. semicarbazones,
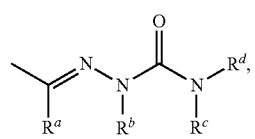

xxiv. thiosemicarbazones,

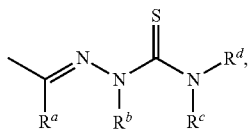

xxv. cyanimide,

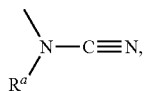

xxvi. hydrazone,

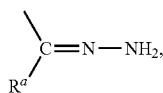

xxvii. oxime,

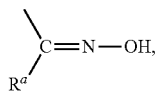

xxviii. nitroamine,

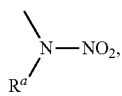

xxix. nitronate,

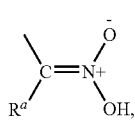

xxx. nitrone,

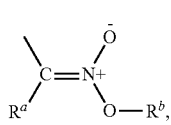

xxxi. carbonates,

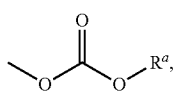

xxxii. carbamates,

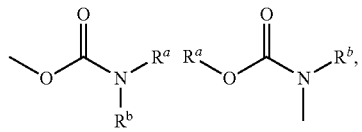

xxxiii. dithiocarbamates,

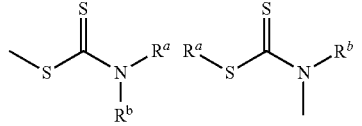

where $R_a$, $R_b$, $R_c$ and $R_d$ in i-xxxiii are independently selected from hydrogen or alkyl ($C_{1-4}$).

In one form of the invention, the invention provides a method for the synthesis of a compound of Formula (1), the method comprising the use of a synthetic intermediate of Formula (4).

In a preferred form of the invention, where V is =, the step of reacting the compound of Formula (4) with one or more other reagents under a second set of reaction conditions to produce the compound of Formula (1) more specifically comprises the step of:

reacting the compound of Formula (4) with a compound of Formula (5);

D-W—R$_1$　　　　　　　　　　　Formula (5)

to produce the compound of Formula (1);
where
D is a halogen, a Group I or Group II metal halide, a triflate or compound $N_2^+BF_4^-$,
W is a benzene or pyridine, and
$R_1$ is independently selected from any one or more of i-xxxiii:
  i. H;
  ii. $C_{1-8}$ alkyl;
  iii. $C_{1-8}$ heteroalkyl;
  iv. carboxylic acids and related derivatives independently selected from:
    a) carboxylic acid,

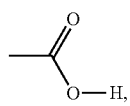

b) alkyl carboxylic acid,

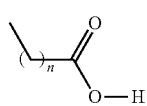

where n=1-8;
    c) thiocarboxylic acid,

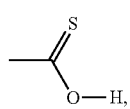

d) alkyl thiocarboxylic acid,

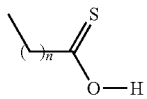

where n=1-8;

e) esters,

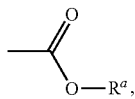

f) alkyl esters,

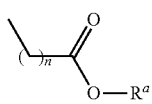

where n=1-8;

g) thioesters,

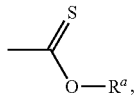

h) alkyl thioesters,

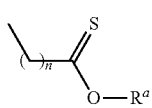

where n=1-8 i) dithioesters,

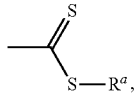

j) alkyl dithioesters,

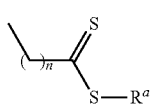

where n=1-8 v. amide derivatives of carboxylic acids independently selected from:

k) amides,

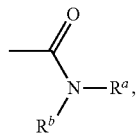

l) thioamides,

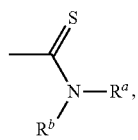

vi. aldehydes, ketones and their derivatives independently selected from:

m) aldehyde,

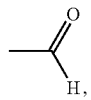

n) thial,

o) ketones,

p) thioketones,

q) acetals,

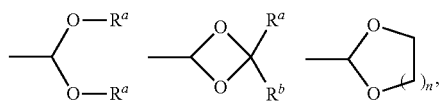

where n=1-3 r) dithioacetals,

[structures: dithioacetal forms with S—R$^a$, S—R$^a$; four-membered with S, S, R$^a$, R$^b$; five-membered dithiolane ()$_n$]

where n=1-3 vii. amines, alkyl amines and their derivatives independently selected from:

s) amines,

[structure: —N(R$^a$)(R$^b$)], t) amides,

[structure: —N(R$^a$)—C(=O)—R$^b$]

u) thioamides,

[structure: —N(R$^a$)—C(=S)—R$^b$]

v) ammonium salts,

[structure: —N$^+$(R$^a$)(R$^b$)(R$^c$)]

w) alkyl amines,

[structure: ( )$_n$—N(R$^a$)(R$^b$)]

where n=1-8 x) alkyl amides,

[structure: ( )$_n$—N(R$^a$)—C(=O)—R$^b$]

where n=1-8 y) alkyl thioamides,

[structure: ( )$_n$—N(R$^a$)—C(=S)—R$^b$]

where n=1-8 z) alkyl ammonium salts,

[structure: ( )$_n$—N$^+$(R$^a$)(R$^b$)(R$^c$)]

where n=1-8, aa) imines,

[structures: —N=C(R$^a$)(R$^b$) and (R$^a$)(R$^b$)C=N—R$^b$]

bb) guanidines,

[structure: —N=C(N(R$^a$)(R$^b$))(N(R$^c$)(R$^d$))]

cc) amidines,

[structure: C(=N—R$^a$)(N(R$^b$)(R$^c$))]

viii. nitrile (cyano), —C≡N,
ix. isonitrile, —N$^+$≡C$^-$,
x. cyanate, —O—C≡N,
xi. isocyanate, —N=C=O,
xii. thiocyanate, —S—C≡N,
xiii. isothiocyanate, —N=C=S,
xiv. azo, —N=NH,
xv. nitro,

[structure: —N$^+$(=O)(O$^-$)], xvi. nitrite, —O—N=O, xvii. nitriso, —N=O,
xviii. N-terminal peptide sequences,

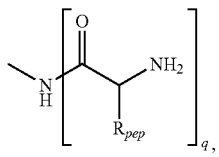

where q=1-3 and $R_{pep}$ is any group resulting in the formation of an amino acid, xix. C-terminal peptide sequences,

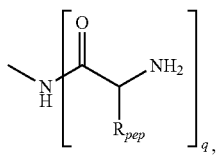

where q=1-3 and $R_{pep}$ is any group resulting in the formation of an amino acid, xx. phosphorus based substituents, where the phosphorus atom is in either the $3^+$ or $5^+$ oxidation state, independently selected from:

dd) alkyl phosphines,

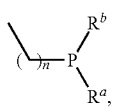

where n=1-8 ee) alkyl phosphonium salts,

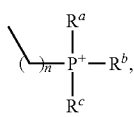

where n=0-8 ff) phosphines,

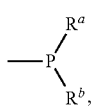

gg) phosphine oxides,

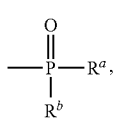

hh) phosphites,

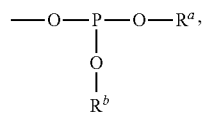

ii) phosphates,

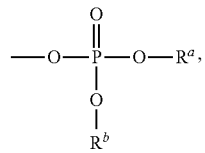

jj) phosphinites,

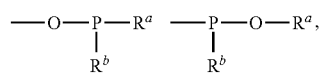

kk) phosphinates,

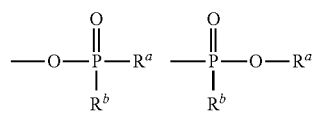

ll) phosphinites,

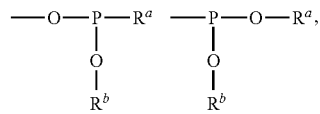

mm) phosphonates,

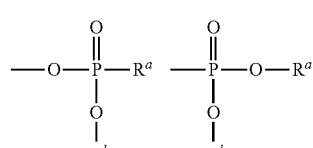

xxi. sulfur based substituents,
nn) sulfate,

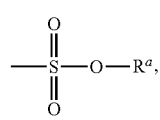

oo) sulfone,
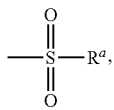
pp) sulfoxide,
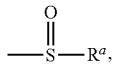
qq) sulfinic acids,
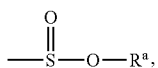
rr) sulfimines,
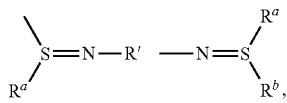
ss) sulfon amides,
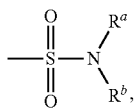
tt) triflates,
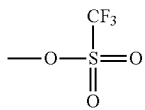
xxii. boron based substituents,
  uu) boronic acid,
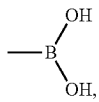
vv) boronic esters,
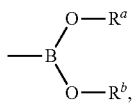
xxiii. semicarbazones,
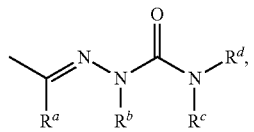
xxiv. thiosemicarbazones,
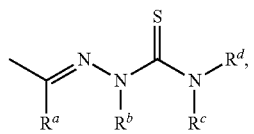
xxv. cyanimide,
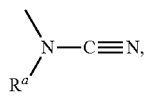
xxvi. hydrazone,
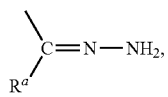
xxvii. oxime,
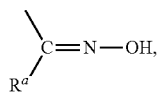
xxviii. nitroamine,
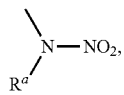
xxix. nitronate,
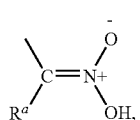
xxx. nitrone,
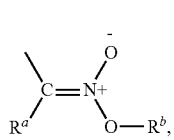

xxxi. carbonates,

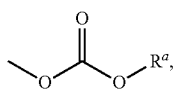

xxxii. carbamates,

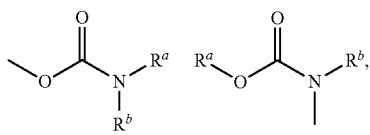

xxxiii. dithiocarbamates,

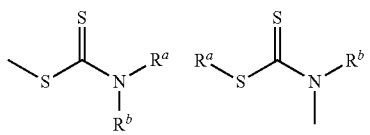

where $R_a$, $R_b$, $R_c$ and $R_d$ in i-xxxiii are independently selected from hydrogen or alkyl ($C_{1-4}$) to produce the compound of Formula (1).

In an alternate form of the invention, where V is ≡, the step of reacting the compound of Formula (4) with one or more other reagents under a second set of reaction conditions to produce the compound of Formula (1) more specifically comprises the steps of:
  reducing the compound of Formula (4) under a third set of reaction conditions to form a compound of Formula (6);

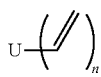

Formula (6)

where
n is 1-6;
U is a benzene or pyridine;
reacting the compound of Formula (6) with a compound of Formula (5)
to produce the compound of Formula (1).

In an alternate form of the invention, where V is the step of reacting the compound of Formula (4) with one or more other reagents under a fourth set of reaction conditions to produce the compound of Formula (1) more specifically comprises the steps of:
  reacting the compound of Formula (4) with the compound of Formula (5) under conditions similar to the second set of reaction conditions to form a compound of Formula (7) and then reacting the compound of Formula (7) under a fourth set of reaction conditions to form the compound of Formula (1);

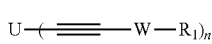

Formula (7)

where
n is 1-6;
U is a benzene or pyridine;
W is a benzene or pyridine;
$R_1$ is independently selected from any one or more of i-xxxiii:
  i. H;
  ii. $C_{1-8}$ alkyl;
  iii. $C_{1-8}$ heteroalkyl;
  iv. carboxylic acids and related derivatives independently selected from:
    a) carboxylic acid,

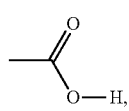

b) alkyl carboxylic acid,

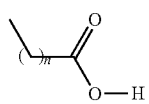

where n=1-8;
    c) thiocarboxylic acid,

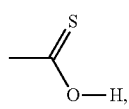

d) alkyl thiocarboxylic acid,

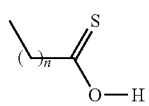

where n=1-8;
    e) esters,

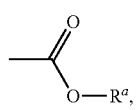

f) alkyl esters,

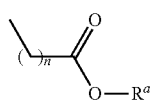

where n=1-8;

g) thioesters,

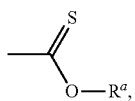

h) alkyl thioesters,

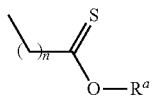

where n=1-8 i) dithioesters,

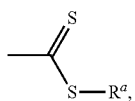

j) alkyl dithioesters,

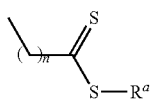

where n=1-8 v. amide derivatives of carboxylic acids independently selected from:

k) amides,

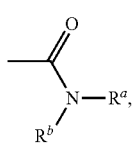

l) thioamides,

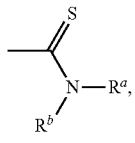

vi. aldehydes, ketones and their derivatives independently selected from:

m) aldehyde,

n) thial,

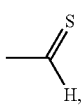

o) ketones,

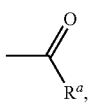

p) thioketones,

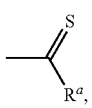

q) acetals,

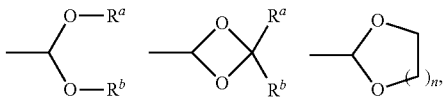

where n=1-3 r) dithioacetals,

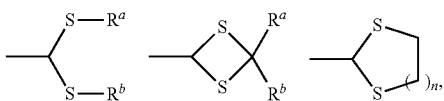

where n=1-3 vii. amines, alkyl amines and their derivatives independently selected from:

s) amines,

t) amides,

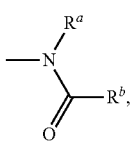

u) thioamides,

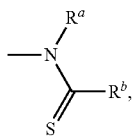

v) ammonium salts,

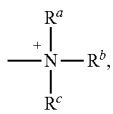

w) alkyl amines,

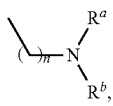

where n=1-8
x) alkyl amides,

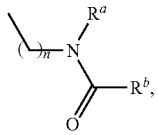

where n=1-8
y) alkyl thioamides,

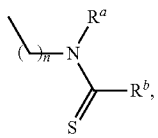

where n=1-8
z) alkyl ammonium salts,

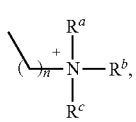

where n=1-8,
aa) imines,

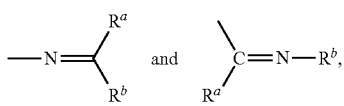

bb) guanidines,

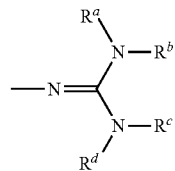

cc) amidines,

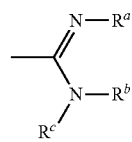

viii. nitrile (cyano), —C≡N,
ix. isonitrile, —N⁺≡C⁻,
x. cyanate, —O—C≡N,
xi. isocyanate, —N=C=O,
xii. thiocyanate, —S—C≡N,
xiii. isothiocyanate, —N=C=S,
xiv. azo, —N=NH,
xv. nitro,

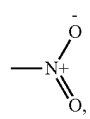

xvi. nitrite, —O—N=O,
xvii. nitriso, —N=O,
xviii. N-terminal peptide sequences,

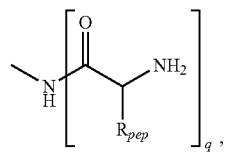

where q=1-3 and $R_{pep}$ is any group resulting in the formation of an amino acid,
xix. C-terminal peptide sequences,

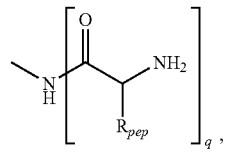

where q=1-3 and $R_{pep}$ is any group resulting in the formation of an amino acid,
xx. phosphorus based substituents, where the phosphorus atom is in either the 3⁺ or 5⁺ oxidation state, independently selected from:

dd) alkyl phosphines,
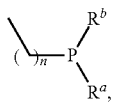
where n=1-8
ee) alkyl phosphonium salts,
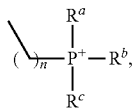
where n=0-8
ff) phosphines,
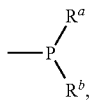
gg) phosphine oxides,
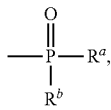
hh) phosphites,
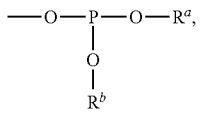
ii) phosphates,
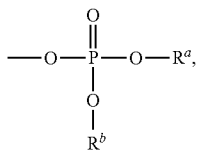
jj) phosphinites,
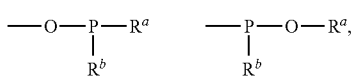
kk) phosphinates,
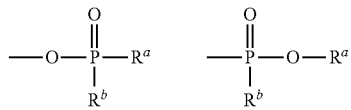
ll) phosphinites,
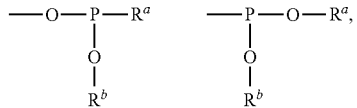
mm) phosphonates,
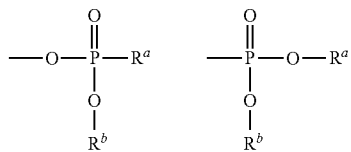
xxi. sulfur based substituents,
nn) sulfate,
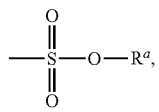
oo) sulfone,
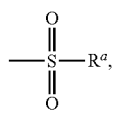
pp) sulfoxide,
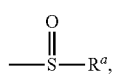
qq) sulfinic acids,
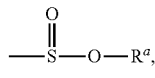
rr) sulfimines,
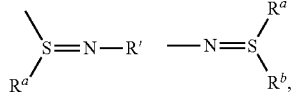

ss) sulfon amides,

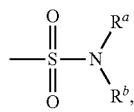

tt) triflates,

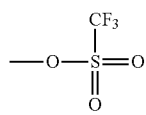

xxii. boron based substituents,
 uu) boronic acid,

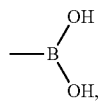

vv) boronic esters,

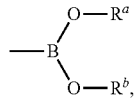

xxiii. semicarbazones,

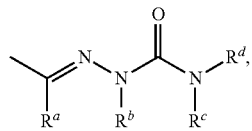

xxiv. thiosemicarbazones,

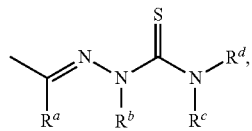

xxv. cyanimide,

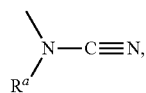

xxvi. hydrazone,

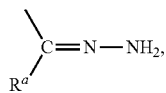

xxvii. oxime,

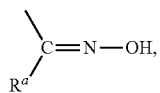

xxviii. nitroamine,

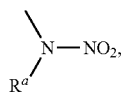

xxix. nitronate,

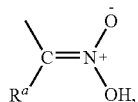

xxx. nitrone,

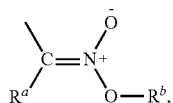

xxxi. carbonates,

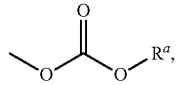

xxxii. carbamates,

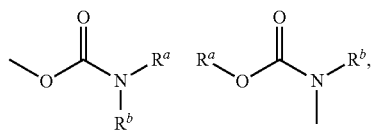

xxxiii. dithiocarbamates,

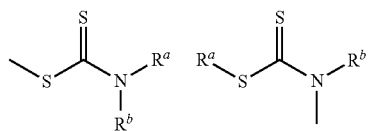

where $R_a$, $R_b$, $R_c$ and $R_d$ in i-xxxiii are independently selected from hydrogen or alkyl ($C_{1-4}$).

In an alternate form of the invention, the step of reacting the compound of Formula (4) with one or more other reagents under a second set of reaction conditions to produce the compound of Formula (1) more specifically comprises the step of:
  reacting the compound of Formula (4) with one or more other reagents under a fifth set of reaction conditions to produce the compound of Formula (8):

U$(-$V$-$X$)_n$         Formula (8)

where
  n is 1-6;
  U is a benzene or pyridine;
  is = or ≡;
  X is a halogen;
  reacting the compound of Formula (8) with a compound of Formula (5) under a sixth set of reaction conditions to produce the compound of Formula (1).

In an alternate form of the invention, where V is the step of reacting the compound of Formula (4) with one or more other reagents under a second set of reaction conditions to produce the compound of Formula (1) more specifically comprises the step of:
  reacting the compound of Formula (4) with one or more other reagents under a seventh set of reaction conditions to produce the compound of Formula (9)

U$-$($\equiv$$-$C$)_n$         Formula (9)

where:
  n is 1-6
  U is a benzene or pyridine;
  C is $Al(CH_3)_2$, $Si(CH_3)_3$, $Si(OCH_3)_3$, $Si(CH_3)_2OH$ or other Group III or Group IV alkyls, alkyl alcohols, ethers or combinations.
  reacting the compound of Formula (9) with a compound of Formula (5) under a eighth set of reaction conditions to produce the compound of Formula (1).

In an alternate form of the invention, the step of reacting the compound of Formula (4) with one or more other reagents under a second set of reaction conditions to produce the compound of Formula (1) more specifically comprises the steps of:
  reacting the compound of Formula (4) with one or more other reagents under a ninth set of reaction conditions to form a compound of Formula (10);

U$(-$V$-$Y$)_n$         Formula (10)

where
  n is 1-6
  U is a benzene or pyridine;
  V is = or ≡;
  Y is $-B^{K-}G_IM^{J+}$;
  G is a halogen;
  M is any Group (I) or Group (II) metal;
  K is 1 or 2;
  I is 3 or 4;
  J is 1 or 2;
  reacting the compound of Formula (10) with a compound of Formula (5) under a tenth set of reaction conditions to produce the compound of Formula (1).

Preferably, each $R_1$ is independently chosen from: an electron-withdrawing group selected from the list comprising:

or a non electron-withdrawing group selected from the list comprising:

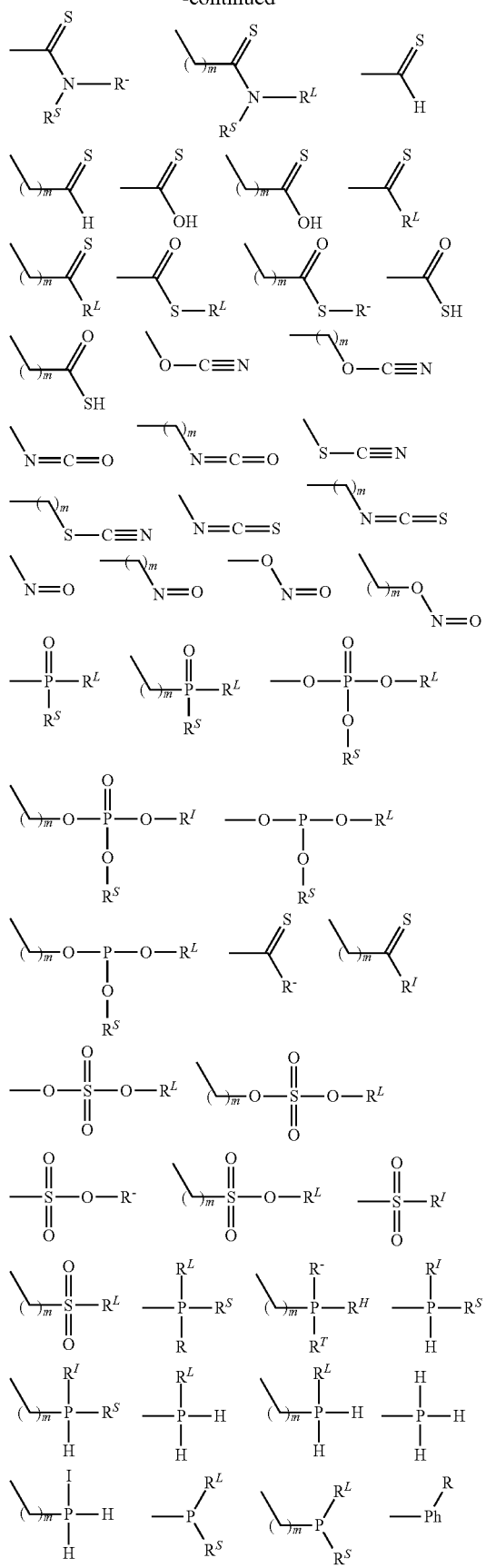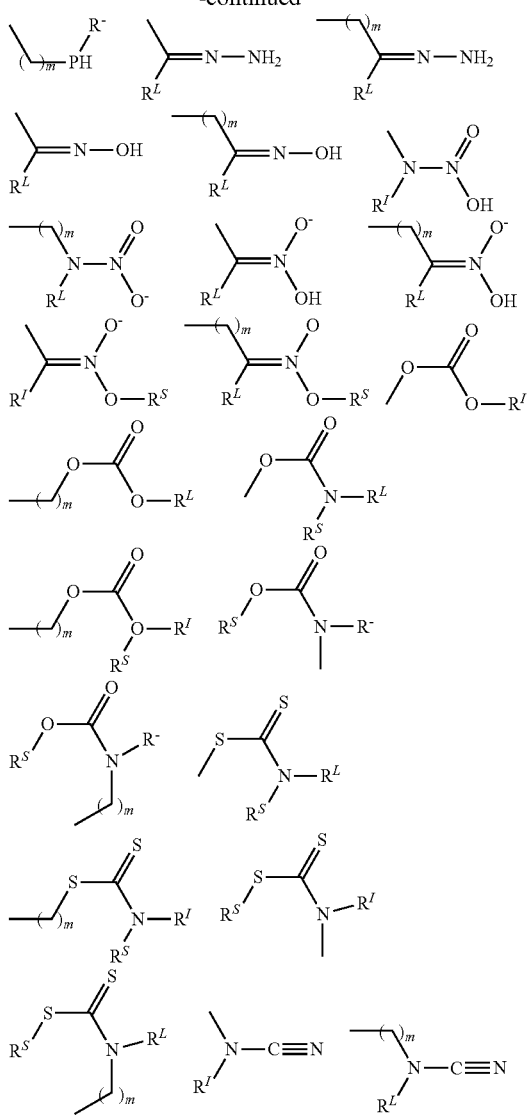

where
m=1-3, $R^L$, $R^S$ and RT are independently selected from hydrogen or alkyl ($C_{1-8}$), E is a triflate or halogen and p=1-3.

Electron-withdrawing group activate the leaving group (D) and facilitate the cross-coupling reaction. Each $R_1$ may independently be any electron-withdrawing group, preferably at least a weak electron-withdrawing group, more preferably at least an intermediate electron-withdrawing group, preferably a strong electron-withdrawing group. There may be a mixture of different strength withdrawing groups within a single compound, as each $R_1$ is chosen independently.

Preferably, at least one $R_1$ is independently chosen from: at least an intermediate electron-withdrawing group selected from the list comprising:

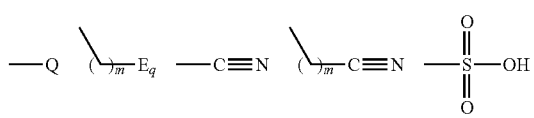

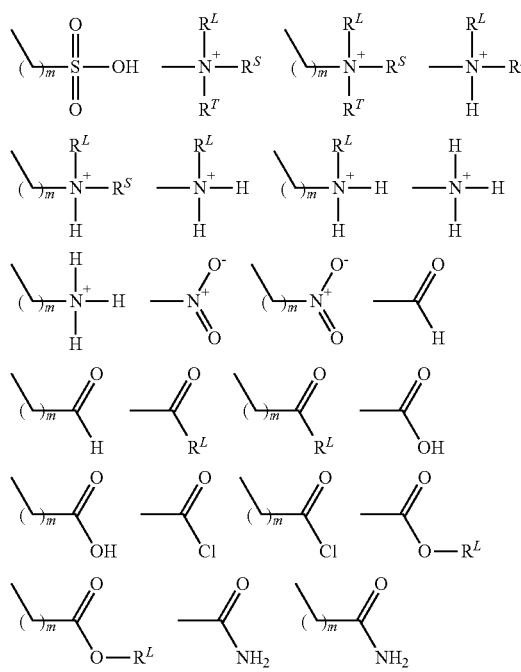

or non electron-withdrawing group selected from the list comprising:

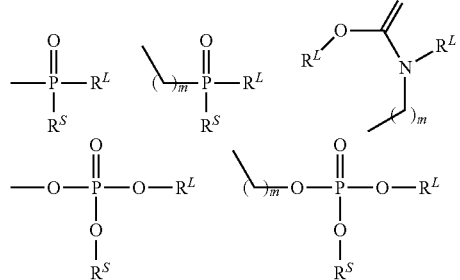

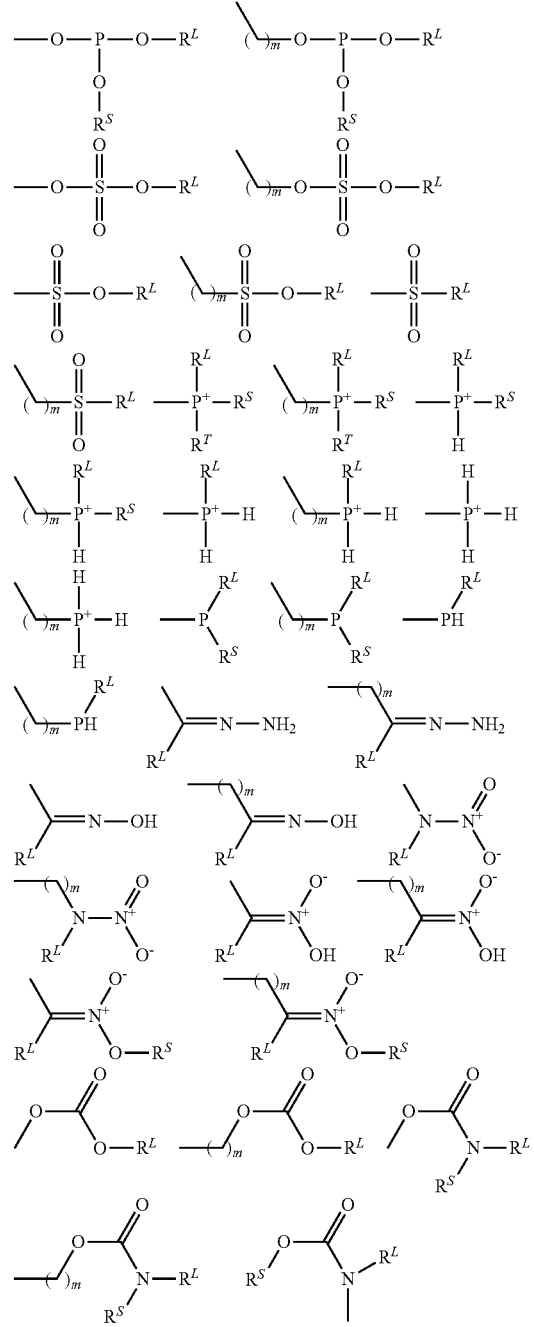

where
m=1-3, $R^L$, $R^S$ and $R^T$ are independently selected from hydrogen or alkyl ($C_{1-8}$), Q is a triflate, E is a triflate or halogen and p=1-3.

In a highly preferred form of the invention, at least one $R_1$ is independently chosen from: a strong electron-withdrawing group selected from the list comprising:

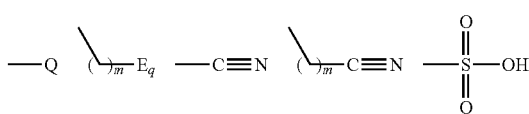

-continued
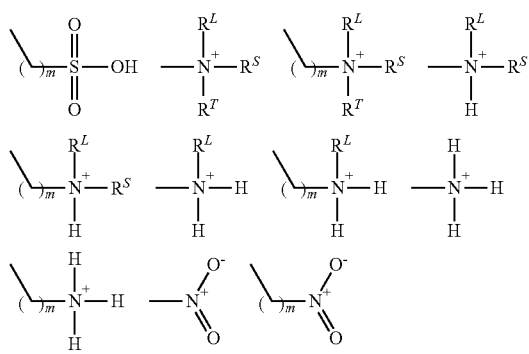
or non electron-withdrawing group selected from the list comprising:
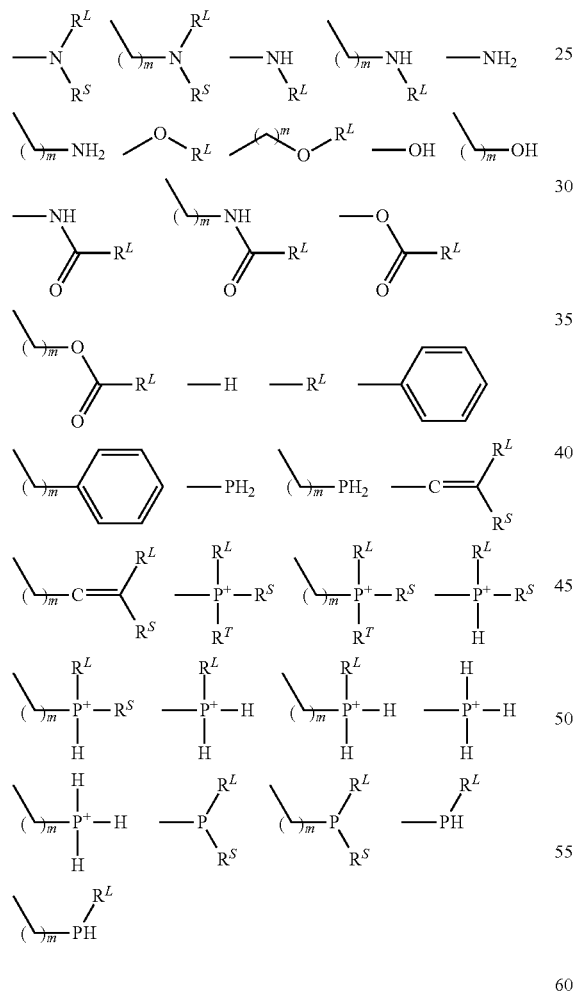
wherein;
m=1-3, $R^L$, $R^S$ and $R^T$ are independently selected from hydrogen or alkyl ($C_{1-8}$), Q is a triflate, E is a triflate or halogen and q=3.
In one form of the invention, the compound of Formula (1) is selected from the group:
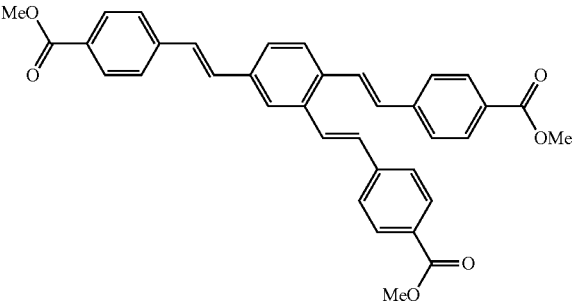
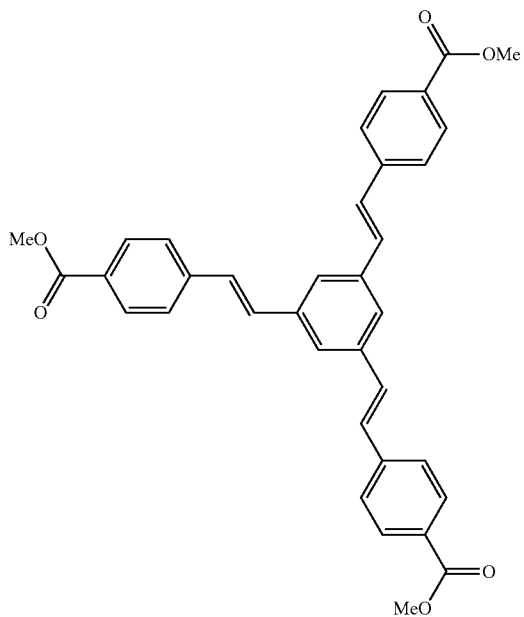
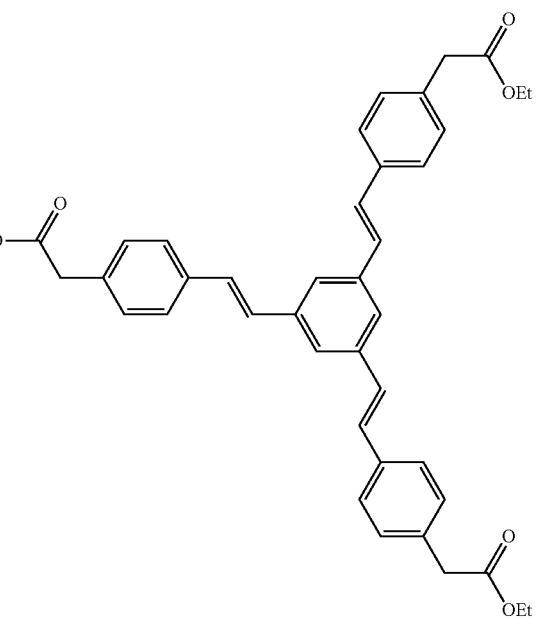

-continued

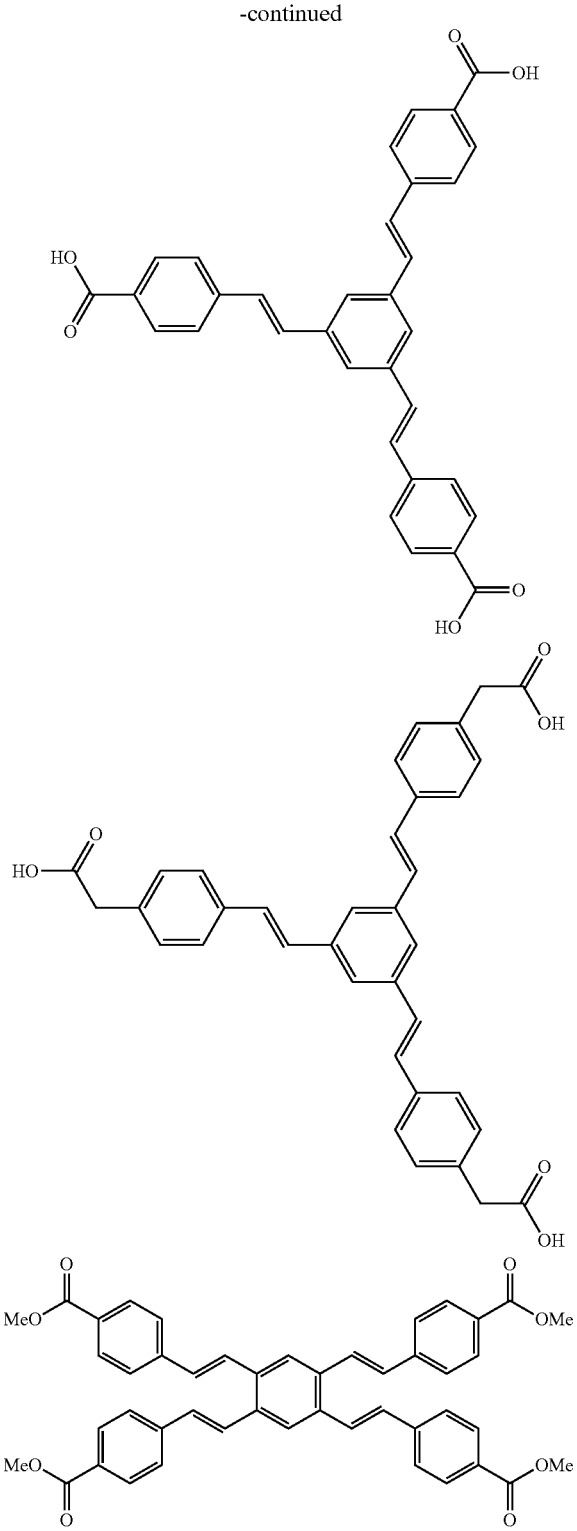

In a highly preferred form of the invention, after the step of reacting a compound of Formula (2) with a compound of Formula (3) under a first set of reaction conditions to produce a compound of Formula (4), and before the step of reacting the compound of Formula (4) with one or more reagents under a second set of reaction conditions to produce the compound of Formula (1), the method comprises the step of:

isolating or concentrating the compound of Formula (4).

In one form of the invention, the step of isolating or concentrating the compound of Formula (4) comprises the following steps:
diluting the reaction mixture with an aqueous diluent;
extracting the reaction mixture with an organic solvent to provide an organic extract;
washing the organic extract with an aqueous solvent to provide a washed organic extract;
drying the washed organic extract to provide a dried extract; and
concentrating the dried organic extract to provide a concentrated extract.

In one form of the invention the aqueous diluent is water.

In one form of the invention, the organic solvent is selected from: ethyl acetate, tetrahydrofuran, dichlormethane, acetone, acetonitrile, dimethylformamide, dimethyl sulfoxide, diethyl ether, 1,4-dioxane, chloroform, toluene, benzene, hexane, notromethane, propylene carbonate, formic acid, n-butanol, isopropanol, n-propanol, ethanol, methanol, acetic acid. Preferably the organic solvent is inexpensive, has low toxicity and/or is easily available in large quantities. Preferably the organic solvent is ethyl acetate.

In one form of the invention, the aqueous solvent is water or brine. In a preferred form of the invention, the method comprises the sequential steps of washing the organic extract with water then brine.

In one form of the invention, the step of drying the washed organic extract to provide a dried extract more specifically comprises contacting the washed organic extract with a compound selected from: anhydrous $Na_2SO_4$, Group I and group II salts of sulphates, chlorides, carbonates and oxides. Preferably the washed organic extract is contacted with a compound capable of drying the organic extract, preferably a compound available in granular form and that is easily removed from the organic extract after drying. Preferably the washed organic extract is contacted with anhydrous $Na_2SO_4$ or $MgSO_4$, more preferably $Na_2SO_4$ (which is available in granular form and is easily removed).

In one form of the invention, the step of isolating or concentrating the compound of Formula (4) comprises the following steps:
purifying the concentrated extract.

In one form of the invention, the step of purifying the concentrated extract comprises purifying the concentrated extract by column chromatography using neat petroleum ether.

In a highly preferred form of the invention, after the step of reacting the compound of Formula (4) with one or more reagents under a second set of reaction conditions to produce the compound of Formula (1), the method comprises the step of:

isolating or concentrating the compound of Formula (1).

In one form of the invention, the step of isolating or concentrating the compound of Formula (1) comprises the following steps:
diluting the reaction mixture with an aqueous diluent;
extracting the reaction mixture with an organic solvent to provide an organic extract;
washing the organic extract with an aqueous solvent to provide a washed organic extract;
drying the washed organic extract to provide a dried extract; and concentrating the dried organic extract to provide a concentrated extract.

In one form of the invention the aqueous diluent is water

In one form of the invention, the organic solvent is chosen from the list comprising: dichloromethane, pentane, cyclopentane, hexane, cyclohexane, benzene, tetrahydrofuran, dichlormethane, acetone, acetonitrile, dimethylformamide, dimethyl sulfoxide, diethyl ether, 1,4-dioxane, chloroform, toluene, benzene, hexane, notromethane, propylene carbonate, formic acid, n-butanol, isopropanol, n-propanol, ethanol, methanol, acetic acid. Preferably the organic solvent is dichloromethane.

In one form of the invention, the aqueous solvent is water or brine. In a preferred form of the invention, the method comprises the sequential steps of washing the organic extract with water then brine.

In one form of the invention, the step of drying the washed organic extract to provide a dried extract more specifically comprises contacting the washed organic extract with a compound selected from: anhydrous $Na_2SO_4$, Group I and group II salts of sulphates, chlorides, carbonates and oxides. Preferably the washed organic extract is contacted with a compound capable of drying the organic extract, preferably a compound available in granular form and that is easily removed from the organic extract after drying. Preferably the washed organic extract is contacted with anhydrous $Na_2SO_4$ or $MgSO_4$, more preferably $Na_2SO_4$ (which is available in granular form and is easily removed).

In one form of the invention, the step of isolating or concentrating the compound of Formula (1) comprises the following steps:
purifying the concentrated extract.

In one form of the invention, the step of purifying the concentrated extract comprises purifying the concentrated extract by column chromatography using petroleum ether/dichloromethane in a ratio of 1:3-1:10, or petroleum ether/ethyl acetate in a ratio of 6:1-3:1.

The step of purifying the concentrated extract may further comprise recrystallizing the compound of Formula (1) using a recrystallization solvent. In a preferred form of the invention, the recrystallization solvent is a mixture of dichloromethane and ethanol in a ratio of 10:1-1:10.

First Set of Reaction Conditions (Formula (2)+Formula (3) to Formula (4))

In one form of the invention, the first set of reaction conditions comprises:
combining 1 equivalent of a compound of Formula (2) with 3-10 equivalents of a compound of Formula (3) in the presence of 0.01-1 equivalents of a catalyst, 2-10 equivalents of a base and optionally 0.01-0.5 equivalents of an ligand in a mixture of an organic solvent and water under an inert atmosphere, to form a reaction mixture.

Preferably the organic solvent is tetrahydrofuran, to form a tetrahydrofuran and water mixture.

Alternatively, the organic solvent in the organic solvent and water mixture is chosen from the list comprising: ethyl acetate, dichloromethane, acetone, acetonitrile, dimethylformamide, dimethyl sulfoxide, diethyl ether, 1,4-dioxane, chloroform, toluene, benzene, hexane, notromethane, propylene carbonate, formic acid, n-butanol, isopropanol, n-propanol, ethanol, methanol, or acetic acid.

If the organic solvent is capable of dissolving both the compound of Formula (2) and the compound of Formula (3), then the presence of water may not be needed. In that case, the mixture of an organic solvent and water may be replaced by an organic solvent alone, where the organic solvent is chosen from the list comprising: tetrahydrofuran, ethyl acetate, dichloromethane, acetone, acetonitrile, dimethylformamide, dimethyl sulfoxide, diethyl ether, 1,4-dioxane, chloroform, toluene, benzene, hexane, notromethane, propylene carbonate, formic acid, n-butanol, isopropanol, n-propanol, ethanol, methanol, or acetic acid.

Alternatively, the organic solvent and water mixture may be replaced with an ionic liquid capable of dissolving the compound of Formula (2) and/or the compound of Formula (3). The ionic liquid may be chosen from the list comprising: A-B where A is the cation and B is the anion. A can be methyl-, ethy-, propy-, butyl-imidazolium or pyridinium, alkyl di-substituted imidazolium or pyridinium, and B can be hexafluorophosphate, tetrafluoroborate, halide, nitrate, sulphate, a Group II metal halide, chlorate, trifluorosulfonate. The ionic liquid can be any imidazole-based or pyridinium-based ionic liquid. The ionic liquid may be used in combination with water to make a ionic liquid and water mixture to dissolve the compounds of Formula (2) and/or the compound of Formula (3).

Preferably, the quantity of the mixture of tetrahydrofuran and water is sufficient to substantially or completely dissolve the material. By substantially, it is preferred that at least 40%, 50%, 60%, 70%, 80%, 90%, 95%, or 98% of the material is dissolved.

In a preferred form of the invention, the first set of reaction conditions further comprises heating the reaction mixture under reflux for a period of 5 to 20 hours. More preferably, the reaction conditions further comprise heating the reaction mixture under reflux for a period of 10 to 19 hours. In a highly preferred form of the invention, the reaction conditions further comprise heating the reaction mixture under reflux for a period of about 16 to 17 hours.

Preferably, the ratio of tetrahydrofuran to water in the mixture of tetrahydrofuran and water is between 10:1 and 1:10. Preferably still, the ratio of tetrahydrofuran to water in the mixture of tetrahydrofuran and water is between 10:1 and 1:1. In a highly preferred form of the invention, the ratio of tetrahydrofuran to water in the mixture of tetrahydrofuran and water is about 9:1.

In a preferred form of the invention, the reaction mixture comprises 3-6 equivalents of the compound of Formula (3). Preferably still, the reaction mixture comprises 3-4.8 equivalents of the compound of Formula (3).

In one form of the invention, the catalyst comprises one or more catalysts selected from the following group: Pd, $PdCl_2$, $Pd(OAc)_2$, $Pd[PPh_3]_4$, $PdCl_2(PPh_3)_2$, $Pd(dba)_2$, $(dppf)PdCl_2$, $Pd_2(dba)_3$, $Pd_2(dba)_3CHCl_3$, $[PdCl(allyl)]_2$, $[PdCl_2(cod)]$, Pd-lysine, Pd-methionine or any other Pd-containing amino acid catalysts. Preferably the catalyst comprises one or more catalysts selected from the following group: $PdCl_2$, $Pd(OAc)_2$, $Pd[PPh_3]_4$, $PdCl_2(PPh_3)_2$, $Pd(dba)_2$, $Pd2(dba)_3$, $Pd_2(dba)_3CHCl_3$. Preferably the catalyst chosen is one that is cheap and/or easily available, so that it may be used for large scale production. Preferably the catalyst comprises $PdCl_2$.

In a preferred form of the invention, the reaction mixture comprises 0.03-0.2 equivalents of the catalyst. Preferably still, the catalyst comprises $PdCl_2$, and the reaction mixture comprises 0.05-0.06 equivalents of the catalyst.

In one form of the invention, the base comprises one or more bases selected from the following group: carbonates, hydroxides, acetates, chlorides, or phosphates of any Group I or Group II metals, organic alcohols, $NH_3$, $Et_3N$, $[HNEt_3][BF_4]$, N-methyldicyclohexylamine, tetra-n-butylammoniumbromide, Brønsted guanidine acid-base ionic liquids, N,N-diisopropylethylamine, or other amine-containing base.

Preferably the base comprises one or more bases selected from the following group: carbonates of any Group I metals, organic alcohols, $NH_3$, $Et_3N$, $[HNEt_3][BF_4]$, N-methyldicyclohexylamine, tetra-n-butylammoniumbromide. Preferably the base chosen is one that is cheap and/or easily available, so that it may be used for large scale production. Preferably the base comprises $Cs_2CO_3$.

In a preferred form of the invention, the reaction mixture comprises 4-8 equivalents of the base. Preferably still, the base comprises $Cs_2CO_3$ and the reaction mixture comprises 4.5-6.0 equivalents of the base.

In one form of the invention, the optional ligand comprises one or more ligands selected from the group: $(tBu)_4NI$, $[(tBu)_3PH]BF_4$, 2-dicylcohexylphosphino-2'-(N,N-dimethylamino)biphenyl, tetrabutylammonium iodide, tetra-n-butylammonium bromide, $tBuPPh_2$, triphenylphosphine, $HBF_4P(tBu)_3$, tri(o-tolyl)phosphine, tris(4,6-dimethyl-3-sulfanatophenyl)phosphine trisodium salt, 1,1-bis(diphenylphosphino)methane, 1,2-bis(dimethylphosphino)ethane, cis,cis,cis-tetrakis(diphylphosphinomethyl)cyclopentane, other phosphine-containing ligands. Preferably the ligand comprises one or more ligands selected from the following group: $(tBu)_4NI$, $[(tBu)_3PH]BF_4$, tetrabutylammonium iodide, tetra-n-butylammonium bromide, $tBuPPh_2$, triphenylphosphine, $HBF_4P(tBu)_3$, tri(o-tolyl)phosphine, Preferably the ligand chosen is one that is cheap and/or easily available, so that it may be used for large scale production. Preferably the ligand comprises $PPh_3$.

In a preferred form of the invention, the reaction mixture comprises 0.05-0.25 equivalents of the ligand. Preferably still, the ligand comprises $PPh_3$ and the reaction mixture comprises 0.15-0.18 equivalents of the ligand.

The reaction mixture may comprise any base selected from those listed above, in combination with any catalyst selected from those listed above. For example, the reaction mixture may comprise one or more bases selected from the following group: carbonates, hydroxides, acetates, chlorides, or phosphates of any Group I or Group II metals, organic alcohols, $NH_3$, $Et_3N$, $[HNEt_3][BF_4]$, N-Methyldicyclohexylamine, tetra-n-butylammoniumbromide, Brønsted guanidine acid-base ionic liquids, N,N-diisopropylethylamine in combination with the catalyst $PdCl_2$. Alternatively, the reaction mixture may comprise one or more catalysts selected from the group: Pd, $PdCl_2$, $Pd(OAc)_2$, $Pd[PPh_3]_4$, $PdCl_2(PPh_3)_2$, $Pd(dba)_2$, (dppf)$PdCl_2$, $Pd_2(dba)_3$, $Pd_2(dba)_3CHCl_3$, $[PdCl(allyl)]_2$, $[PdCl_2(cod)]$, Pd-lysine, Pd-methionine or any other Pd-containing amino acid catalysts in combination with the base $Cs_2CO_3$. Preferably, the reaction mixture comprises the catalyst $PdCl_2$ and the base $Cs_2CO_3$. The reaction mixture may further comprise an ligand, chosen from the list comprising $(tBu)_4NI$, $[(tBu)_3PH]BF_4$, 2-dicylcohexylphosphino-2'-(N,N-dimethylamino)biphenyl, tetrabutylammonium iodide, tetra-n-butylammonium bromide, $tBuPPh_2$, triphenylphosphine, $HBF_4P(tBu)_3$, tri(o-tolyl)phosphine, tris(4,6-dimethyl-3-sulfanatophenyl)phosphine trisodium salt, 1,1-bis(diphenylphosphino)methane, 1,2-bis(dimethylphosphino)ethane, cis,cis,cis-tetrakis(diphylphosphinomethyl)cyclopentane, other phosphine-containing ligands; preferably $PPh_3$.

Second Set of Reaction Conditions (Formula (4) or (6)+ Formula (5) to Formula (1))

Preferably, where the method of the invention comprises the step of reacting the compound of Formula (4) or (6) with a compound of Formula (5), the second set of reaction conditions comprises:

combining 1 equivalent of a compound of Formula (4) or (6) with 3-10 equivalents of a compound of Formula (5) in the presence of 0.01-1 equivalents of a catalyst, 1-15 equivalents of a base and optionally 1-10 equivalents of an ligand in dry dimethylformamide under an inert atmosphere, to form a reaction mixture.

Preferably the dry dimethylformamide is anhydrous and/or distilled.

Alternatively, the dimethylformamide may be replaced with one or more compounds chosen from the list comprising: tetrahydrofuran, dichlormethane, acetone, acetonitrile, dimethylformamide, dimethyl sulfoxide, diethyl ether, 1,4-dioxane, chloroform, toluene, benzene, hexane, notromethane, propylene carbonate, formic acid, n-butanol, isopropanol, n-propanol, ethanol, methanol, acetic acid.

Preferably, the quantity of the dry dimethylformamide is sufficient to substantially or completely dissolve the material. By substantially, it is preferred that at least 40%, 50%, 60%, 70%, 80%, 90%, 95%, or 98% of the material is dissolved.

In a preferred form of the invention, the second set of reaction conditions further comprise heating the reaction mixture at a temperature of between 60° C. and 150° C. for a period of 5 to 20 hours. Preferably still, the second set of reaction conditions further comprise heating the reaction mixture at a temperature of between 70° C. and 130° C. for a period of 10 to 19 hours. Preferably still, the second set of reaction conditions further comprise heating the reaction mixture at a temperature of between 80° C. and 100° C. for a period of about 16 to 17 hours.

In a preferred form of the invention, the reaction mixture comprises 3-8 equivalents of the compound of Formula (5). Preferably still, the reaction mixture comprises 3.3-6 equivalents of the compound of Formula (5).

In one form of the invention, the catalyst comprises one or more catalysts selected from the following group: Pd, $PdCl_2$, $Pd(OAc)_2$, $Pd[PPh_3]_4$, $PdCl_2(PPh_3)_2$, $Pd(dba)_2$, (dppf)$PdCl_2$, $Pd2(dba)_3$, $Pd_2(dba)_3CHCl_3$, $[PdCl(allyl)]_2$, $[PdCl_2(cod)]$, Pd-lysine, Pd-methionine or any other Pd-containing amino acid catalysts. Preferably the catalyst comprises one or more catalysts selected from the following group: $PdCl_2$, $Pd(OAc)_2$, $Pd[PPh_3]_4$, $PdCl_2(PPh_3)_2$, $Pd(dba)_2$, $Pd2(dba)_3$, $Pd_2(dba)_3CHCl_3$. Preferably the catalyst chosen is one that is cheap and/or easily available, so that it may be used for large scale production. Preferably the catalyst comprises $Pd(OAc)_2$.

In a preferred form of the invention, the reaction mixture comprises 0.01-1 equivalents of the catalyst. Preferably still, the catalyst comprises $Pd(OAc)_2$, and the reaction mixture comprises 0.05-0.15 equivalents of the catalyst. In alternative form of the invention, the catalyst comprises $Pd_2(dba)_3CHCl_3$ and the reaction mixture comprises 0.01-0.05 equivalents of the catalyst, or 0.025 equivalents of the catalyst.

In one form of the invention, the base comprises one or more bases selected from the following group: carbonates, hydroxides, acetates, chlorides, or phosphates of any Group I or Group 11 metals, organic alcohols, $NH_3$, $Et_3N$, $[HNEt_3][BF_4]$, N-methyldicyclohexylamine, tetra-n-butylammoniumbromide, Brønsted guanidine acid-base ionic liquids, N,N-diisopropylethylamine or any other amine-containing catalyst. Preferably the base comprises one or more bases selected from the following group: carbonates of any Group 1 metals, organic alcohols, $NH_3$, $Et_3N$, $[HNEt_3][BF_4]$, N-methyldicyclohexylamine, tetra-n-butylammoniumbromide. Preferably the base chosen is one that is cheap and/or easily available, so that it may be used for large scale production. Preferably the base comprises triethylamine, $K_2CO_3$ and/or LiCl.

In a preferred form of the invention, the reaction mixture comprises 3-15 equivalents of the base. Preferably still, the base comprises triethylamine and the reaction mixture comprises 4-12 equivalents of the base. In an alternate form of the invention, the base comprises $K_2CO_3$ and the reaction mixture comprises 10 equivalents of the base. In an alternate form of the invention, the base comprises LiCl and the reaction mixture comprises 6 equivalents of the base.

In one form of the invention, the optional ligand comprises one or more ligands selected from the group: $(tBu)_4NI$, $[(tBu)_3PH]BF_4$, 2-dicylcohexylphosphino-2'-(N,N-dimethylamino)biphenyl, tetrabutylammonium iodide, tetra-n-butylammonium bromide, $tBuPPh_2$, triphenylphosphine, $HBF_4P(tBu)_3$, tri(o-tolyl)phosphine, tris(4,6-dimethyl-3-sulfanatophenyl)phosphine trisodium salt, 1,1-bis(diphenylphosphino)methane, 1,2-bis(dimethylphosphino)ethane, cis,cis,cis-tetrakis(diphylphosphinomethyl)cyclopentane, other phosphine-containing ligands. Preferably the ligand comprises one or more ligands selected from the following group: $(tBu)_4NI$, $[(tBu)_3PH]BF_4$, tetrabutylammonium iodide, tetra-n-butylammonium bromide, $tBuPPh_2$, triphenylphosphine, $HBF_4P(tBu)_3$, tri(o-tolyl)phosphine, Preferably the ligand chosen is one that is cheap and/or easily available, so that it may be used for large scale production. Preferably the ligand comprises $n-Bu_4NI$.

In a preferred form of the invention, the reaction mixture comprises 1-5 equivalents of the ligand. In a form of the invention, the ligand comprises $n-Bu_4NI$ and the reaction mixture comprises 2 equivalents of the ligand.

In a highly preferred form of the invention, where the compound of Formula (1) is 1,2,4-tris[(1E)-2'-(methyl 4"-benzoate)vinyl]benzene, or triethyl 2,2',2"-{[(1E,1'E,1"E)-benzene-1,3,5-triyltris(ethene-2,1-diyl)]tris(benzene-4,1-diyl)}triacetate, the reaction mixture comprises (i) a catalyst in the form of $Pd(OAc)_2$ in a relative quantity of 0.05-0.15 equivalents, and (ii) a base in the form of triethylamine in a relative quantity of 10.0 equivalents.

In a highly preferred form of the invention, where the compound of Formula (1) is 1,3,5-tris[(1E)-2'-(methyl 4"-benzoate)vinyl]benzene, the reaction mixture comprises (i) a catalyst in the form of $Pd(OAc)_2$ in a relative quantity of 0.05-0.15 equivalents, (ii) a base in the form of a mixture of $K_2CO_3$ and LiCl in a relative quantity of 10 equivalents and 6 equivalents respectively, and (iii) an ligand in the form of $n-Bu_4NI$ in a relative quantity of 2 equivalents.

In a highly preferred form of the invention, where the compound of Formula (1) is 1,2,4,5-tetrakis[(1E)-2'-(methyl 4"-benzoate)vinyl]benzene, the reaction mixture comprises (i) a catalyst in the form of $Pd_2(dba)_3CHCl_3$ in a relative quantity of 0.025 equivalents, and (ii) a base in the form of triethylamine in a relative quantity of 10.0 equivalents.

Third Set of Reaction Conditions (Reduction)

A range of different methods are available and well understood by the skilled reader to reduce the optional triple bond of Formula 4, when it is an alkyne, to a double bond. Some non-limiting examples are provided.

To the alkyne (1 eq), polymethylhydrosiloxane (PMHS) (1.2 eq), IPrCuOtBu (0.5 mol-%) and iBuOH (1.2 eq) are added in toluene and the reaction stirred at 25° C. for 1 h to produce a compound of Formula 6. See, for example, A. M Whittaker, G. Lalic, Org. Lett., 2013, 15, 1112-1115. This method is preferred as it provides good yields from large scale production.

To the alkyne (1 eq), $InCl_3$ (2 eq), $Et_3SiH$ (2 eq), $Et_3B$ (0.1 eq) (1M in hexane) are added in acetonitrile and the reaction stirred at 0° C. for 2 h to produce compound of Formula 6. See, for example, N. Hayashi, I. Shibata, A. Baba, Org. Lett., 2004, 6, 4981-4983.

Fourth Set of Reaction Conditions (Reduction)

A range of different methods are available and well understood by the skilled reader to reduce the triple bond of the alkyne of Formula 7 to a double bond. Some non-limiting examples are provided.

To the alkyne (1 eq), $Pd_2(dba)_3$ (1 mol-%), dppb (4 mol-%), $HCO_2H$ (25% aqueous, 2 eq) are added in dioxane and the reaction stirred at 80° C. for 10 h to produce a compound of Formula 1. See, for example, R. Shen, T. Chen, Y. Zhao, R. Qiu, Y. Zhou, S. Yin, X. Wang, M. Goto, L.-B. Han, J. Am. Chem. Soc., 2011, 133, 17037-17044.

To the alkyne (1 eq), $RuCl_2(PPh)_3$ (2.5 mol-%), CuI (0.1 eq), Zn (2 eq), $H_2O$ (8 eq) were added in dioxane and the reaction stirred at 100° C. for 36 h to produce compound of Formula 1. See, for example, T. Schabel, C. Belger, B. Plietker, Org. Lett., 2013, 15, 2858-2861.

To the alkyne (1 eq), PMHS (1.2 eq), IPrCuOtBu (0.5 mol-%) and iBuOH (1.2 eq) are added in toluene and the reaction stirred at 25° C. for 1 h to produce a compound of Formula 1. See, for example, A. M Whittaker, G. Lalic, Org. Lett., 2013, 15, 1112-1115.

To the alkyne (1 eq), $Pd(OAc)_2$ (2 mol-%), KOH (1.5 eq) are added in dimethylformamide and the reaction stirred at 145° C. for 6-9 h to produce a compound of Formula 1. See, for example, J. Li, R. Hua, T. Liu, J. Org. Chem., 2010, 75, 2966-2970. This method is preferred as it provides a cost-effective method for large-scale production.

Fifth Set of Reaction Conditions (Formula (4) to Formula (8))

A range of different methods are available and well understood by the skilled reader for the synthesis of a vinyl halide from a vinyl. A non-limiting example is provided.

To a compound of Formula 4 (1 eq), vinyl trimethyl silcon was added in the presence of $RuH(Cl)(CO)(PPh_3)_3$ (1 mol-%) in toluene and the reaction heated at 100° C. for 6 hr to produce the intermediate. N-iodosuccinimide or N-bromosuccinimide (1.2 eq) was added in the presence of MeCN/toluene in a ratio of 4:1 and the reaction stirred at room temperature for 1 h to produce a compound of Formula 8. See, for example, P. Pawluć, G. Hreczycho, J. Szudkowska, M. Kubicki, B. Marciniec, Org. Lett., 2009, 11, 3390-3393.

Sixth Set of Reaction Conditions (Formula (8)+Formula (5) to Formula (1))

A range of different methods are available and well understood by the skilled reader for the synthesis of a compound of Formula (1) from a compound of Formula (8). A non-limiting example is provided.

To a compound of Formula (8) (1 eq), a compound of Formula (5) (1.2 eq) was added in the presence of $Pd(dba)_2$ (0.1 mol-%) and $Cs_2CO_3$ (2 eq) in methanol and the reaction stirred at room temperature for 12 hr to produce a compound of Formula (1). See, for example, J. S. Tang, M. Tian, W. B. Sheng, C. C. Guo, Synthesis, 2012, 44, 541-546.

Seventh Set of Reaction Conditions (Formula (4) to Formula (9))

A range of different methods are available and well understood by the skilled reader to produce a compound of Formula (9) from a compound of Formula (4). A non-limiting example is provided.

To a compound of Formula (4) (1 eq), $Al(CH_3)_3$ (1.1 eq, 2M in heptane) was added in the presence of triethylamine (0.1 eq) and the reaction stirred at 60° C. for 6 hr to produce a compound of Formula (9). See, for example, B. Wang, M. Bonin, L. Micouin, Org. Lett., 2004, 6, 3481-3484.

Eighth Set of Reaction Conditions (Formula (9)+Formula (5) to Formula (1))

A range of different methods are available and well understood by the skilled reader to produce a compound of Formula (1) from a compound of Formula (9). Some non-limiting examples are provided.

To a compound of Formula 9 (1.5 eq in heptane), a compound of Formula 5 (1 eq) is added in the presence of $Pd_2(dba)_3 \cdot CHCl_3$ (2.5 mol-%) and dppf (5 mol-%) in dimethoxyethane and the reaction stirred at 20° C. or 85° C. for 0.5-5 hr to produce a compound of Formula (1). See, for example, B. Wang, M. Bonin, L. Micouin, Org. Lett., 2004, 6, 3481-3484. This method is preferred as it is rapid and uses minimal reagents.

To a compound of Formula 9 (1.2 eq in heptane), a compound of Formula 5 (1 eq) is added in the presence of $Pd(PPh_3) \cdot CHCl_3$ (2 mol-%), CuI (2 mol-%), $PPh_3$ (4 mol-%) in toluene/$iPr_2NH_2$ (5:1) at 25° C. or 80° C. for 16 hr to produce an intermediate which was then reacted with KOH (6 eq, 2.4 M in $H_2O$/MeOH 5:1) at 25° C. for 3 hr after which a compound of Formula 5 (1 eq) was added and the reaction stirred at 25° C. for 16 hr to produce a compound of Formula (1). See, for example, R. Severin, J. Reimer, S. Doye, J. Org. Chem., 2010, 75, 3518-3521.

Ninth Set of Reaction Conditions (Formula (4) to Formula (10))

A range of different methods are available and well understood by the skilled reader to produce a compound of Formula (10) from a compound of Formula (4). A non-limiting example is provided.

To a compound of Formula 4 (1 eq), n-BuLi (1 eq) is added in tetrahydrofuran at −78° C. and the reaction stirred for 1 hr after which, $B(OCH_3)_3$ (1.5 eq) is added at −78° C. for 1 hr and then the temperature is raised to −20° C. for an additional hour. Finally $KHF_2$ (6 eq, saturated in $H_2O$) was added at −20° C. and the reaction stirred for 1 hr and then an additional 1 hr at room temperature to produce a compound of Formula (10). See, for example, G. A. Molander, B. W. Katona, F. Machrouhi, J. Org. Chem., 2002, 67, 8416-8423. This method is preferred as it is rapid and uses minimal reagents.

Tenth Set of Reaction Conditions (Formula (10)+Formula (5) to Formula (1))

A range of different methods are available and well understood by the skilled reader to produce a compound of Formula (1) from a compound of Formula (10). A non-limiting example is provided.

To a compound of Formula (10) (1 eq), a compound of Formula (5) (1 eq) is added in the presence of $PdCl_2(dppf) \cdot CHCl_2$ (2 mol-%), $tBuNH_2$ (3 eq), iPrOH/$H_2O$ at a ratio of 1:1 and the reaction heated to reflux for 2-24 hr to produce a compound of Formula (1). See, for example, G. A. Molander, C. R. Bernardi, J. Org. Chem., 2002, 67, 8424-8429. This method is preferred as it is rapid and uses minimal reagents.

Scale

In a preferred form of the invention, the method of the invention is performed at large scale. As used herein, the term large scale refers to a reaction that utilises at least about five moles of at least one starting material. Preferably, a large scale process utilises at least about 0.1, 1, 10, 20, 50, 100, 500 or 1000 moles of at least one starting material.

Compounds and Methods

The present invention further comprises compounds produced by the methods of the present invention.

The present invention further comprises salts, including pharmaceutically acceptable salts, of compounds produced by the methods of the present invention.

Pharmaceutically acceptable salts for the purposes of the present invention include non-toxic cation and anion salts. Examples include, but are not limited to sodium, potassium, aluminium, calcium, lithium, magnesium, zinc and from bases such as ammonium, ethylenediamine, N-methyl-glutamine, lysine, arginine, ornithine, choline, N, N'-dibenzylethylenediamine, diethylamine, piperazine, tris(hydroxymethyl)aminomethane, tetramethylammonium, acetate, lactobionate, benzenesulfonate, laurate, benzoate, malate, bicarbonate, maleate, bisulfate, mandelate, bitratrate, meyate, borate, methylbromide, bromide, methylnitrate, calcium edetate, methylsulfate, camsylate, mucate, carbonate, napsylate, chloride, nitrate, clavulanate, N-methylglucamine, citrate, hydrochloride, oleate, edetate, oxalate, edisylate, pamoate (embonate), estolate, palmitate, esylate, pantothenate, fumarate, phosphate, diphosphate, glucepate, plygalacturonate, gluconate, salicylate, glutamate, stearate, glycollylarsanilate, sulfate, hexylresorcinate, subacetate, hydrabamine, succinate, hydrobromide, tannate, tartrate, hydroxynapthoate, teoclate, iodide, tosylate, isothionate, triethiodide, lactate, panoate and valerate.

The present invention further comprises use of a compound of Formula (1) produced by the method of the present invention or analogues thereof, or pharmaceutically acceptable salts thereof in the manufacture of a medicament for the therapeutic treatment of bacterial infection or disease in a subject in need thereof, wherein the bacterial infection or disease results from Gram-positive bacteria.

The present invention further comprises use of a compound of Formula (1) produced by the method of the present invention or analogues thereof, or pharmaceutically acceptable salts thereof in a pharmaceutical composition.

The precise composition of the present invention will vary according to a wide range of commercial and scientific criteria. Methods for the preparation of pharmaceutical compositions comprising one or more active ingredients are generally known in the art. Such compositions will generally be formulated for the mode of delivery that is to be used and will usually include one or more pharmaceutically acceptable carriers.

Generally, examples of suitable carriers, excipient and diluents include, without limitation, water, saline, ethanol, dextrose, glycerol, lactose, dextrose, sucrose, sorbitol, mannitol, starches, gum acacia, calcium phosphates, alginate, tragacanth, gelatine, calcium silicate, microcrystalline cellulose, polyvinylpyrrolidone, cellulose, water syrup, methyl cellulose, methyl and propylhydroxybenzoates, polysorbates, talc magnesium stearate, mineral oil or combinations thereof. The formulations can additionally include lubricating agents, pH buffering agents, wetting agents, emulsifying and suspending agents, preserving agents, sweetening agents or flavouring agents.

Topical formulations

The pharmaceutical composition may be adapted for topical application. In this regard, various topical delivery systems may be appropriate for administering the compositions of the present invention depending up on the preferred treatment regimen. Topical formulations may be produced by dissolving or combining the compound of the present invention in an aqueous or non aqueous carrier. In general, any liquid, cream, or gel or similar substance that does not appreciably react with the compound or any other of the active ingredients that may be introduced into the composition and which is non-irritating is suitable. Appropriate non-sprayable viscous, semi-solid or solid forms can also be employed that include a carrier compatible with topical application and have dynamic viscosity preferably greater than water.

Suitable formulations are well known to those skilled in the art and include, but are not limited to, solutions, suspensions, emulsions, creams, gels, ointments, powders, liniments, salves, aerosols, transdermal patches, etc, which are, if desired, sterilised or mixed with auxiliary agents, e.g. preservatives, stabilisers, emulsifiers, wetting agents, fragrances, colouring agents, odour controllers, thickeners such as natural gums, etc. Particularly preferred topical formulations include ointments, creams or gels.

Ointments generally are prepared using either (1) an oleaginous base, i.e., one consisting of fixed oils or hydrocarbons, such as white petroleum, mineral oil, or (2) an absorbent base, i.e., one consisting of an anhydrous substance or substances which can absorb water, for example anhydrous lanolin. Customarily, following formation of the base, whether oleaginous or absorbent, the active ingredient is added to an amount affording the desired concentration.

Creams are oil/water emulsions. They consist of an oil phase (internal phase), comprising typically fixed oils, hydrocarbons and the like, waxes, petroleum, mineral oil and the like and an aqueous phase (continuous phase), comprising water and any water-soluble substances, such as added salts. The two phases are stabilised by use of an emulsifying agent, for example, a surface active agent, such as sodium lauryl sulfite; hydrophilic colloids, such as acacia colloidal clays, veegum and the like. Upon formation of the emulsion, the compound can be added in an amount to achieve the desired concentration.

Gels comprise a base selected from an oleaginous base, water, or an emulsion-suspension base. To the base is added a gelling agent that forms a matrix in the base, increasing its viscosity. Examples of gelling agents are hydroxypropyl cellulose, acrylic acid polymers and the like. Customarily, the compound is added to the formulation at the desired concentration at a point preceding addition of the gelling agent.

The amount of compound incorporated into a topical formulation is not critical; the concentration should be within a range sufficient to permit ready application of the formulation such that an effective amount of the compound is delivered.

Oral Formulations

The pharmaceutical composition may be adapted for oral delivery. In this regard, the compound can be administered as an oral preparation adapted in such a manner that facilitates delivery of a therapeutically effective concentration of the compound.

The effective dosages of the compound, when administered orally, must take into consideration the diluent, preferably water. The composition preferably contains 0.05% to about 100% by weight active ingredient and more preferably about 10% to about 80% by weight. When the compositions are ingested, desirably they are taken on an empty stomach.

Contemplated for use herein are oral solid dosage forms including tablets, capsules, pills, troches or lozenges, cachets or pellets. Also, liposomal or proteinoid encapsulation may be used to formulate the present compositions. Liposomal encapsulation may be used and the liposomes may be derivatised with various polymers. In general, the formulation will include the compound and inert ingredients that allow for protection against the stomach environment and release of the biologically active material in the intestine.

The location of release may be the stomach, the small intestine (the duodenum, the jejunum, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the composition or by release of the compound beyond the stomach environment, such as in the intestine.

To ensure full gastric resistance, a coating impermeable to at least pH 5.0 may be used. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S and Shellac. These coatings may be used as mixed films.

A coating or mixture of coatings that are not intended for protection against the stomach can also be used on tablets. This can include sugar coatings, or coatings that make the tablet easier to swallow. Capsules may consist of a hard shell (such as gelatine) for delivery of dry therapeutic i.e. powder; for liquid forms, a soft gelatine shell may be used. The shell material of cachets could be thick starch or other edible paper. For pills, lozenges, moulded tablets or tablet triturates, moist massing techniques can be used.

One may dilute or increase the volume of the composition with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the compound into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatine, orange peel, acid carboxymethyl cellulose, natural sponge and bentonite may all be used. Another form of the disintegrants is insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the composition together to form a hard tablet and include materials from natural products such as acacia, tragacanth, starch and gelatine. Others include methylcellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the compound.

An antifrictional agent may be included in the formulation to prevent sticking during the formulation process. Lubricants may be used as a layer between the compound and the die wall and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights and Carbowax 4000 and 6000.

Glidants that might improve the flow properties of the composition during formulation and to aid rearrangement during compression might be added. The glidants may include starch, talc, pyrogenic silica and hydrated silicoaluminate.

To aid dissolution of the compound, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation either alone or as a mixture in different ratios.

Controlled release formulations may be desirable. The compounds can be incorporated into an inert matrix that permits release by either diffusion or leaching mechanisms i.e., gums. Slowly degenerating matrices may also be incorporated into the formulation. Another form of a controlled release formulation is by a method based on the Oros therapeutic system (Alza Corp.), i.e. the composition is enclosed in a semipermeable membrane which allows water to enter and push the composition out through a single small opening due to osmotic effects. Some enteric coatings also have a delayed release effect.

A mix of materials might be used to provide the optimum film coating. Film coating may be carried out in a pan coater or in a fluidised bed or by compression coating.

The compound can be included in the formulation as fine multi-particulates in the form of granules or pellets of particle size about 1 mm. The formulation of the material for capsule administration could also be as a powder, lightly compressed plugs or even as tablets. The compound could be prepared by compression.

Injectable Formulations

The compound can also be formulated for parenteral delivery. Pharmaceutical forms suitable for injectable use include: sterile aqueous solutions (where water-soluble) or dispersions and sterile powders for the extemporaneous preparation of sterile injectable solutions or dispersion. Alternatively, the compounds of the invention may be encapsulated in liposomes and delivered in injectable solutions to assist their transport across cell membrane. The solution may be a solvent or dispersion medium containing, for example, water, ethanol, polyol (for example, glycerol, propylene glycol and liquid polyethylene glycol and the like), suitable mixtures thereof and vegetable oils. Proper fluidity may be maintained, for example, by the use of a coating such as lecithin, by the maintenance of the required particle size in the case of dispersion and by the use of surfactants. Prolonged absorption of the injectable compositions can be brought about by the use in the compositions of agents delaying absorption, for example, aluminium monostearate and gelatine.

Sterile injectable solutions may be prepared by incorporating the active compounds in the required amount in an appropriate solvent with various of the other ingredients enumerated above, as required, followed by filtered sterilisation. Generally, dispersions are prepared by incorporating the compound into a sterile vehicle that contains the basic dispersion medium and the other ingredients. In the case of sterile powders for the preparation of sterile injectable solutions, the preferred methods of preparation are vacuum drying and freeze-drying techniques that yield a powder of the compound plus any additional desired ingredient from previously sterile-filtered solution thereof.

Thus, the present invention also provides an injectable, stable, sterile composition comprising a compound of Formula A, or a salt thereof, in a unit dosage form in a sealed container. The compound or salt may be provided in lyophilised form capable of being reconstituted with a suitable pharmaceutically acceptable carrier to form a liquid composition suitable for injection thereof into a subject. The unit dosage form typically comprises from about 10 mg to about 10 grams of the compound or salt thereof. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Aerosols

Pharmaceutical compositions are also provided which are suitable for administration as an aerosol, by inhalation. These compositions comprise a solution or suspension of the desired compound or a salt thereof or a plurality of solid particles of the compound or salt. The desired composition may be placed in a small chamber and nebulized. Nebulization may be accomplished by compressed air or by ultrasonic energy to form a plurality of liquid droplets or solid particles comprising the compounds or salts.

The solid particles can be obtained by processing solid compound or a salt thereof, in any appropriate manner known in the art, such as by micronization. Commercial nebulizers are also available to provide liquid droplets of any desired size.

The liquid droplets or solid particles should have a particle size in the range of about 0.5 to about 5 microns, preferably from about 1 to about 2 microns. Most preferably, the size of the solid particles or droplets will be from about 1 to about 2 microns. Such particles or droplets may be dispensed by commercially available nebulisers or by other means known to the skilled person.

When the pharmaceutical composition suitable for administration as an aerosol is in the form of a liquid, the composition will comprise a water-soluble form of the compound or a salt thereof, in a carrier that comprises water. A surfactant may be present which lowers the surface tension of the composition sufficiently to result in the formation of droplets within the desired size range when subjected to nebulization.

In addition, the pharmaceutical composition may also include other agents. For example, preservatives, co-solvents, surfactants, oils, humectants, emollients, chelating agents, dyestuffs, stabilizers or antioxidants may be employed. Water soluble preservatives that may be employed include, but are not limited to, benzalkonium chloride, chlorobutanol, thimerosal, sodium bisulfate, phenylmercuric acetate, phenylmercuric nitrate, ethyl alcohol, methylparaben, polyvinyl alcohol, benzyl alcohol and phenylethyl alcohol. The surfactant may preferably be polysorbate 80. Other suitable additives include lubricants and slip agents, such as, for example, magnesium stearate, stearic acid, talc and bentonites, substances which promote disintegration, such as starch or cross linked polyvinylpyrrolidone, binders, such as, for example, starch, gelatin or linear polyvinylpyrrolidone, and dry binders, such as microcrystalline cellulose.

Other vehicles that may be used include, but are not limited to, polyvinyl alcohol, povidone, hydroxypropyl methyl cellulose, poloxamers, carboxymethyl cellulose, hydroxyethyl cellulose, purified water, etc. Tonicity adjustors may be included, for example, sodium chloride, potassium chloride, mannitol, glycerin, etc. Antioxidants include, but are not limited to, sodium metabisulfite, sodium thiosulfate, acetylcysteine, butylatedhydroxyanisole, butylated hydroxytoluene, etc. The indications, effective doses, compositions, contraindications, vendors etc, of the compounds in the compositions are available or are known to one skilled in the art. These agents may be present in individual amounts of from about 0.001% to about 5% by weight and preferably about 0.01% to about 2%.

Electrolytes such as, but not limited to, sodium chloride and potassium chloride may also be included in the composition.

Further, the compositions may contain microbial preservatives. Useful microbial preservatives include methylparaben, propylparaben, benzyl alcohol, phenoxyethanol and hydroxyacetophenone. The microbial preservative is typically employed when the composition is placed in a vial designed for multidose use.

Excipients which may be used are all the physiologically acceptable solid inert substances, either inorganic or organic in nature. Inorganic substances are, for example, sodium chloride, carbonates, such as calcium carbonate, bicarbonates, aluminium oxides, silicic acids, aluminas, precipitated or colloidal silicon dioxide and phosphates. Organic substances are, for example, sugars, cellulose, foodstuffs and feedstuffs, such as milk powder, animal flours, cereal flours and shredded cereals and starches.

Finally, it will be appreciated that the compositions of the present invention may comprise a plurality of compounds as described herein.

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

As used herein the term "derived" and "derived from" shall be taken to indicate that a specific integer may be obtained from a particular source albeit not necessarily directly from that source.

As used herein, the singular forms "a," "an" and "the" include plural references unless the context clearly dictates otherwise.

Throughout this specification, unless the context requires otherwise, the word "comprise", or variations such as "comprises" or "comprising", will be understood to imply the inclusion of a stated integer or group of integers but not the exclusion of any other integer or group of integers.

Other than in the operating example, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

Examples

Examples of the present invention are illustrated with reference to the following synthetic scheme. The numerals identifying compounds in the synthetic scheme are used consistently in the following descriptions of syntheses.

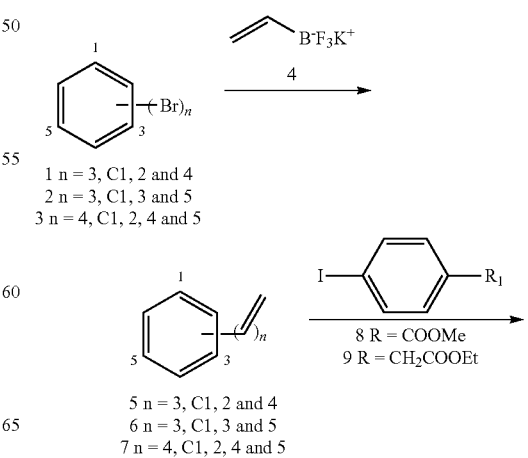

-continued

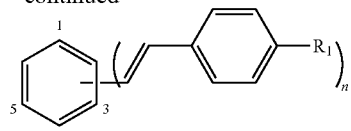

10 R = COOMe, n = 3, C1, 2 and 4
11 R = COOMe, n = 3, C1, 3 and 5
12 R = COOMe, n = 4, C1, 2, 4 and 5
13 R = CH$_2$COOEt, n = 3, C1, 3 and 5

Synthesis of Compound 5

A suspension of compound 1 (27.0 g, 85.7 mmol), potassium vinyltrifluoroborate (compound 4) (41.4 g, 0.31 mol), PdCl$_2$ (0.76 g, 4.3 mmol), Cs$_2$CO$_3$ (125.6 g, 0.39 mol) and PPh$_3$ (3.38 g, 12.9 mmol) in a mixture of THF and water (400 mL, THF/H$_2$O 9:1) was heated at reflux for 17 h under a nitrogen atmosphere. The reaction was cooled to room temperature and the solvent removed by evaporation. The residue obtained was diluted with water (300 mL) and extracted with ethyl acetate (100 mL×3). The combined organic extracts were washed with water (200 mL) and brine (100 mL), dried (Na$_2$SO$_4$) and concentrated to give the crude product, which was purified by column chromatography (neat petroleum ether), illustrated in FIG. 1, to afford compound 5 (11.40 g, 85%) as an oil.

Synthesis of Compound 6

Figure 2:
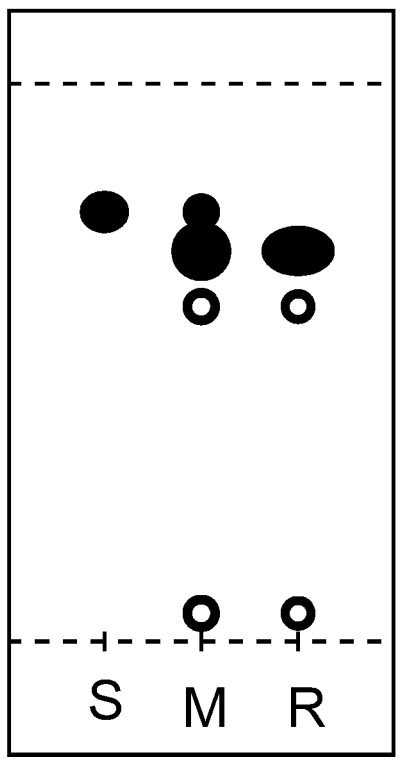
FIG. 2 illustrates column chromatography of compound 6 as described in the Examples.

A suspension of compound 2 (11.6 g, 36.8 mmol), potassium vinyltrifluoroborate (compound 4) (14.8 g, 0.11 mol), PdCl$_2$ (0.39 g, 2.2 mmol), Cs$_2$CO$_3$ (72.0 g, 0.22 mol) and PPh$_3$ (1.73 g, 6.6 mmol) in a mixture of THF and water (200 mL THF/H$_2$O=9:1) was heated at reflux under a nitrogen atmosphere 16 h. The reaction was cooled to room temperature and the solvent removed reduced pressure. The residue obtained was diluted with 300 mL water and extracted with ethyl acetate (60 mL×3). The combined organic extracts were washed with water (200 mL) and brine (100 mL), dried (Na$_2$SO$_4$) and concentrated to give a crude product, which was purified by column chromatography (neat petroleum ether), illustrated in FIG. 2, to give pure compound 6 (5.40 g, 90%) as an oil.

Synthesis of Compound 7

Figure 3:
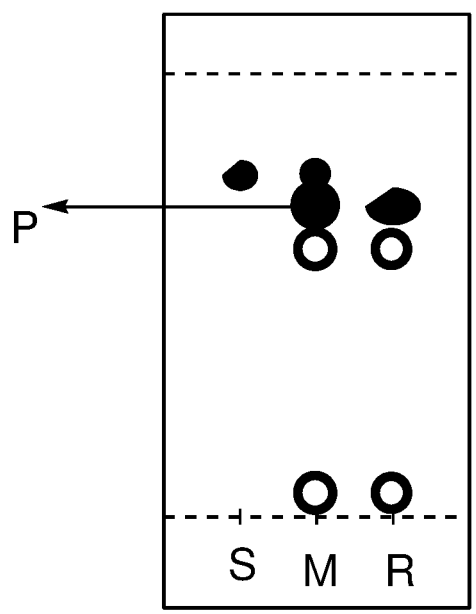
FIG. 3 illustrates column chromatography of compound 7 as described in the Examples.

A suspension of compound 3 (20.0 g, 50.8 mmol), potassium vinyltrifluoroborate (compound 4) (32.7 g, 0.24 mol), PdCl$_2$ (0.45 g, 2.5 mmol), Cs$_2$CO$_3$ (99.3 g, 0.31 mol) and PPh$_3$ (2.00 g, 7.6 mmol) in a mixture of THF and water (400 mL, THF/H$_2$O 9:1) was heated at reflux for 17 h under a nitrogen atmosphere. The reaction was cooled to room temperature and the solvent removed under reduced pressure. The residue obtained was diluted with water (300 mL) and extracted with ethyl acetate (100 mL×3). The combined organic extracts were washed with water (200 mL) and brine (100 mL), dried (Na$_2$SO$_4$) and concentrated. The crude product obtained was purified by column chromatography (neat petroleum ether), illustrated in FIG. 3, to give compound 7 (7.00 g, 75%) as an oil.

Synthesis of Compound 10

Figure 4:
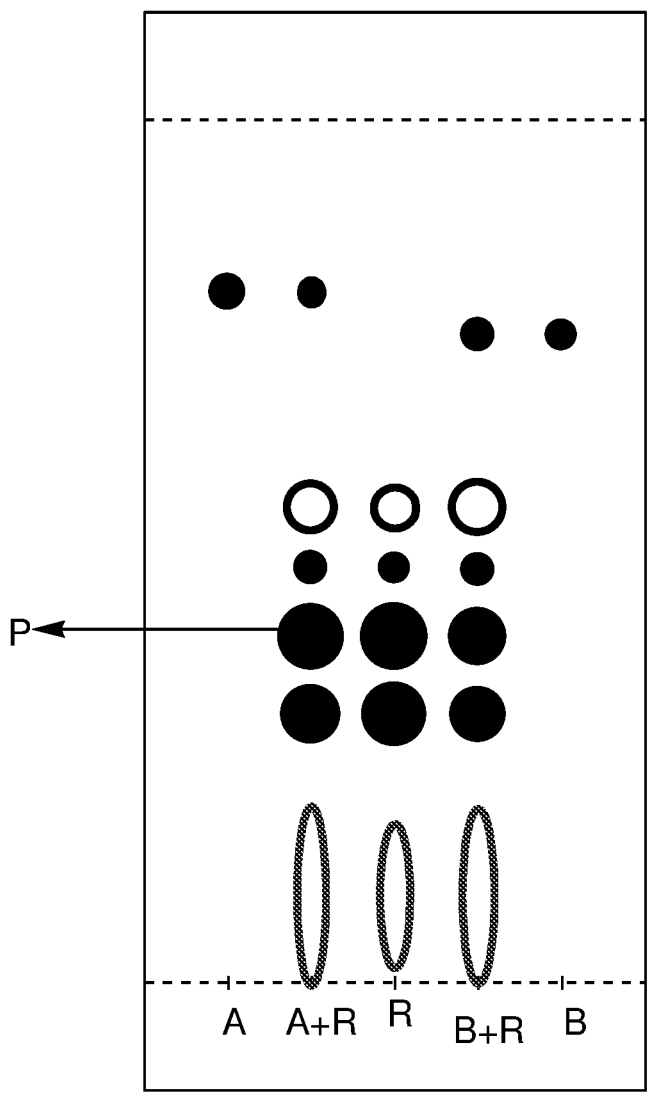
FIG. 4 illustrates column chromatography of compound 10 as described in the Examples.

A suspension of compound 5 (11.40 g, 72.9 mmol), methyl 4-iodobenzoate (compound 8) (86.0 g, 0.33 mol), Pd(OAc)$_2$ (0.82 g, 3.65 mmol), Et$_3$N (73.9 g, 0.73 mol) in 160 mL dry DMF was heated to 100° C. under nitrogen atmosphere for 17 h. The mixture was then cooled to room temperature and diluted with 1000 ml water and extracted with dichloromethane (3×300 mL). The extracts washed with water (200 mL) and brine (100 mL), dried (Na$_2$SO$_4$) and concentrated. The crude product was purified by column chromatography (petroleum ether/dichloromethane 1:3-1:10), illustrated in FIG. 4, to give compound 6 (12.6 g) as a yellow solid. This material was further purified by recrystallization (DCM/EtOH 1:8), to afford compound 10 (11.5 g, 28%).

Synthesis of Compound 11

Figure 5:
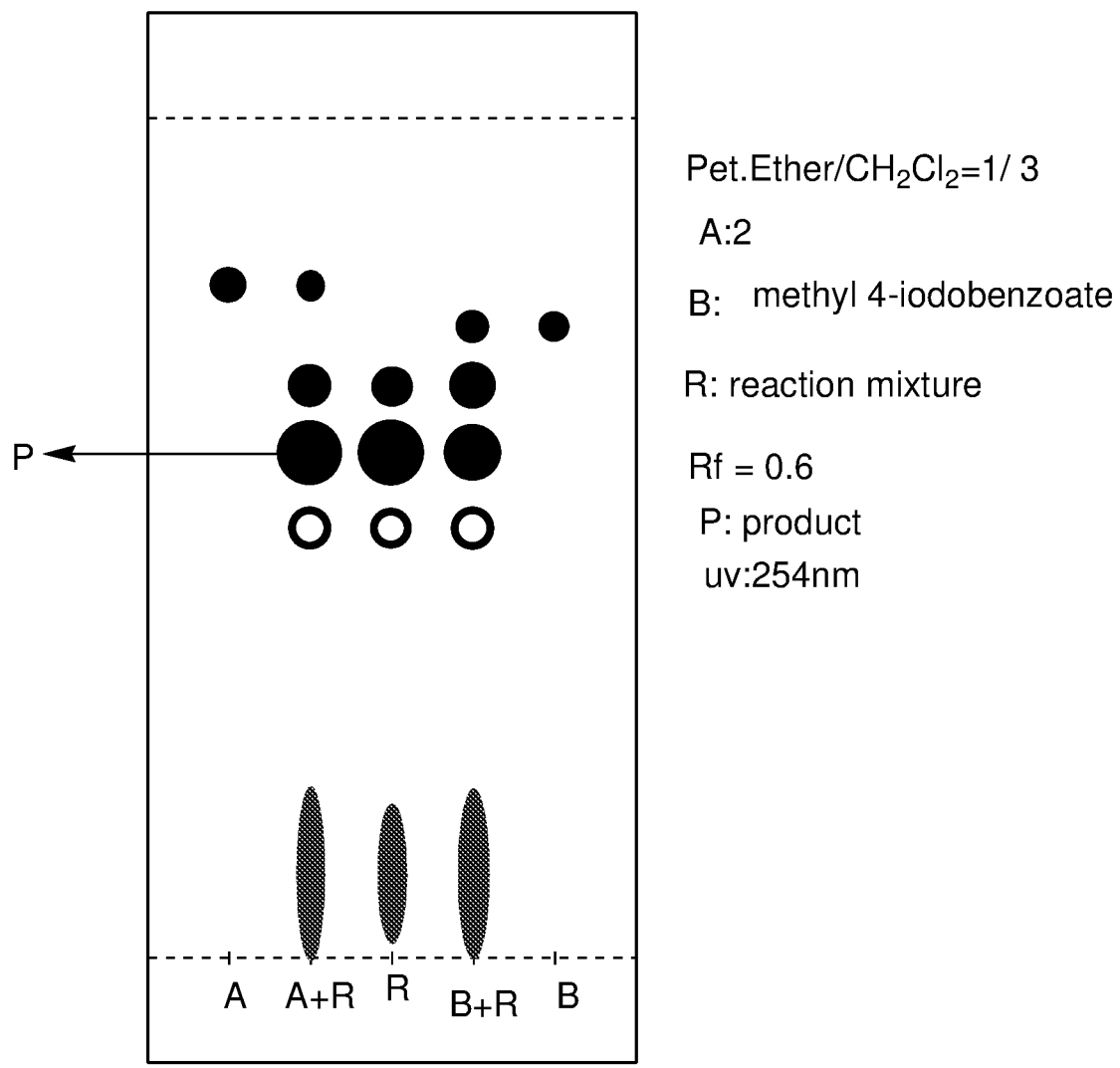
FIG. 5 illustrates column chromatography of compound 11 as described in the Examples.

A suspension of compound 6 (4.68 g, 30.0 mmol), methyl 4-iodobenzoate (compound 8) (26.0 g, 99.0 mmol), Pd(OAc)$_2$ (1.00 g, 4.5 mmol), K$_2$CO$_3$ (41.4 g, 0.30 mol), LiCl (7.68 g, 0.18 mol) and n-Bu$_4$NI (22.1 g, 60.0 mmol) in 160 mL dry DMF was heated at 100° C. under a nitrogen atmosphere 17 h. The reaction was cooled to room temperature, diluted with 1000 mL water and extracted with dichloromethane (3×300 mL). The combined organic extracts were washed with water (200 mL) and brine (100 mL), dried (Na$_2$SO$_4$) and concentrated to give a crude product, which was purified by column chromatography (petroleum ether/dichloromethane 1:31:10), illustrated in FIG. 5, to give compound 11 (7.0 g, 40%) as a grey/white solid.

Synthesis of Compound 12

Figure 6:
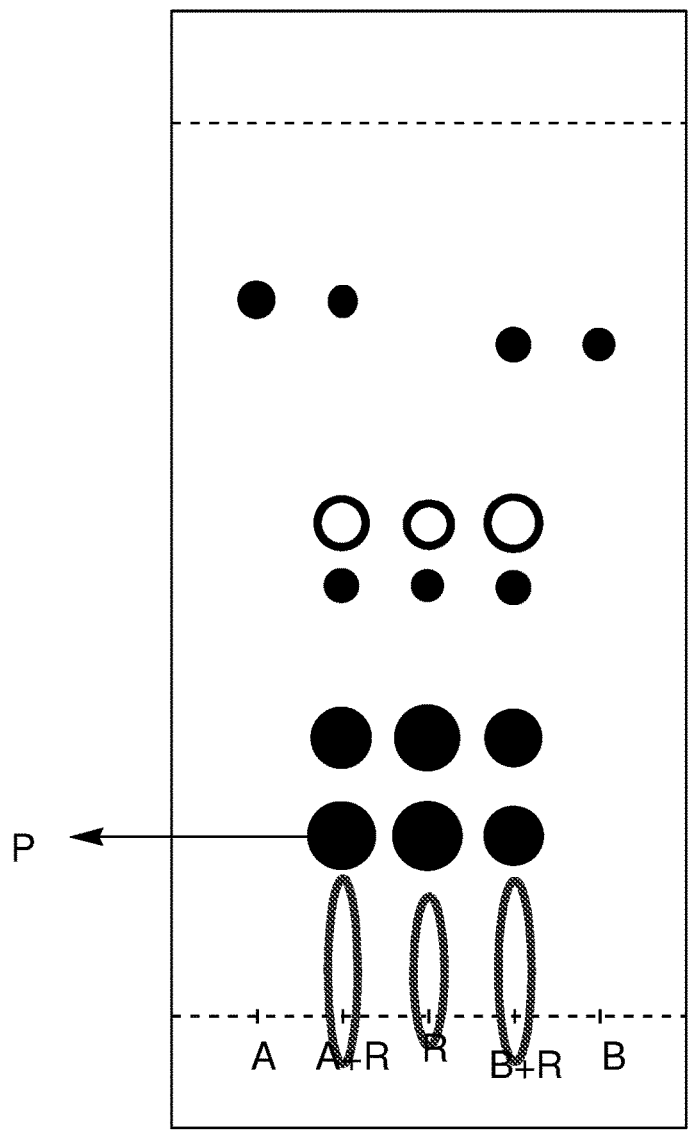
FIG. 6 illustrates column chromatography of compound 12 as described in the Examples.

A suspension of compound 7 (5.30 g, 29.0 mmol), methyl 4-iodobenzoate (compound 8) (47.0 g, 0.18 mol), Pd$_2$(dba)$_3$·CHCl$_3$ (0.78 g, 0.75 mmol) and Et$_3$N (30.3 g, 0.30 mol) in dry DMF (100 mL) was heated at 80° C. for 17 h under a nitrogen atmosphere. The reaction was cooled to room temperature and diluted with water (1000 mL). The aqueous layer was extracted with dichloromethane (3×300 mL) and the combined organic extract washed with water (200 mL) and brine (100 mL), dried (Na$_2$SO$_4$) and concentrated. The crude product obtained was purified by column chromatography (petroleum ether/dichloromethane 1:3-1:10, then dichloromethane/MeOH$_2$ 00:1), illustrated in FIG. 6, to give compound 12 (7.0 g, 35%) as a yellow solid.

Synthesis of Compound 13

Figure 7:
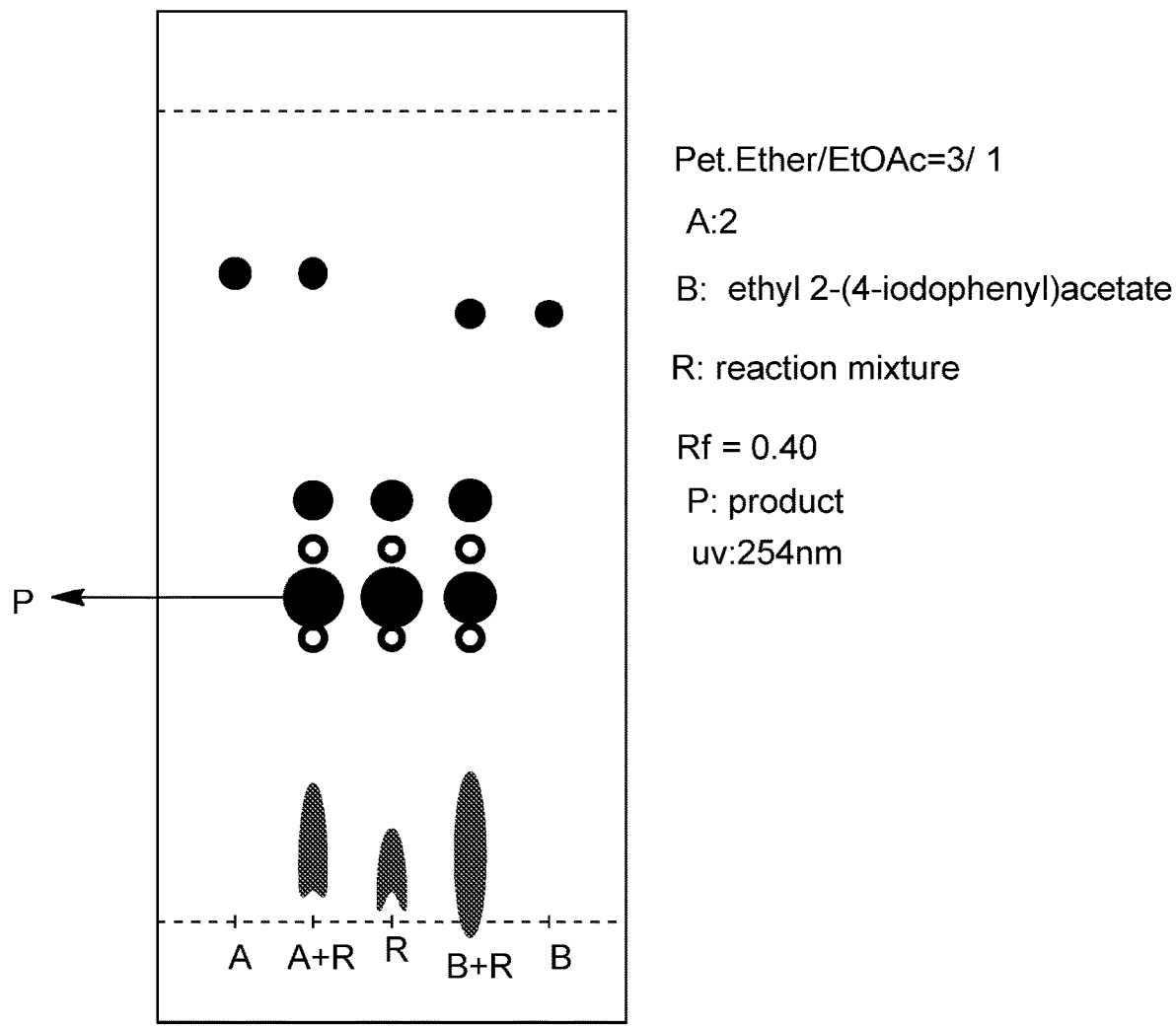
FIG. 7 illustrates column chromatography of compound 13 as described in the Examples.

A suspension of compound 6 (4.13 g, 26.5 mmol), ethyl 2-(4-iodophenyl)acetate (compound 9) (28.0 g, 95.3 mmol), Pd(OAc)$_2$ (0.59 g, 2.65 mmol), and Et$_3$N (27.0 g, 0.27 mol) in 150 mL dry DMF was heated at 100° C. under a nitrogen atmosphere for 17 h. The reaction was cooled to room temperature and diluted with water (500 mL). The pH of the aqueous solution was adjusted to 1 by addition of 2M HCl and the aqueous layer extracted with ethyl acetate (4×300 mL). The combined organic extracts were washed with water (3×500 mL) and brine (500 mL), dried using Na$_2$SO$_4$ and concentrated to give a crude product, which was purified by column chromatography (petroleum ether/ethyl acetate 6:1 to 3:1), illustrated in FIG. 7, to provide compound 13 (10.3 g, 42%) as a yellow solid.

Modifications of the above-described modes of carrying out the various embodiments of this invention will be apparent to those skilled in the art based on the above teachings related to the disclosed invention. The above embodiments and examples of the invention are included solely for the purposes of exemplifying the present invention

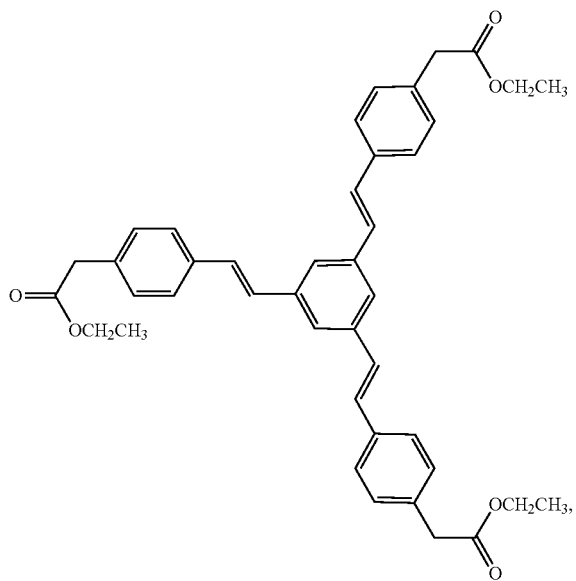

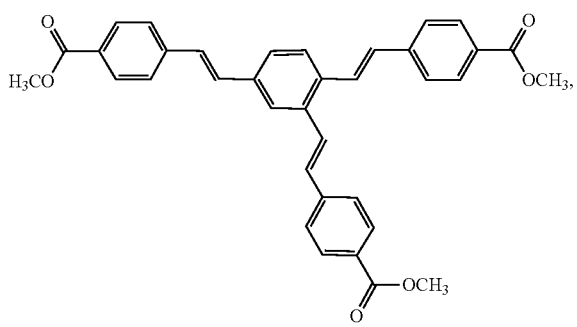

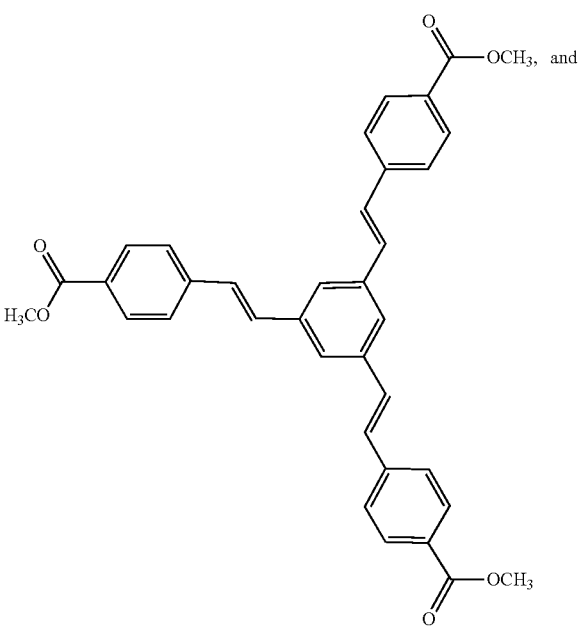

-continued
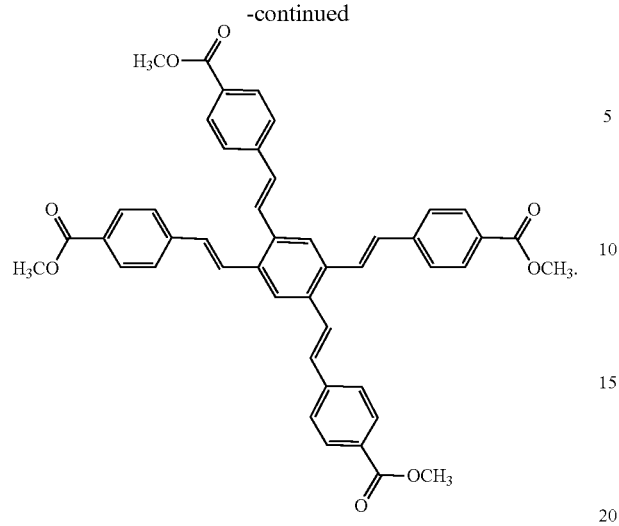

The invention claimed is:

1. A process for the synthesis of a compound of Formula (1):

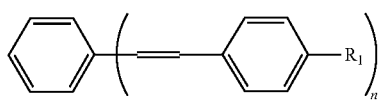
Formula (1)

wherein:
n is 2, 3, or 4;
each $R_1$ is independently —$(CH_2)_mC(O)OR^a$ or —$C(O)OR^a$;
each $R^a$ is independently $C_{1-4}$ alkyl; and
m is 1, 2, 3, 4, 5, 6, 7, or 8;
wherein the process comprises the following steps:
(i) reacting a compound of Formula (2):

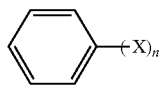
Formula (2)

wherein:
n is 2, 3, or 4; and
X is a halogen;
with a compound of Formula (3):

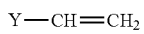
Formula (3)

Y—CH=$CH_2$ wherein:
Y is —$BF_3^-K^+$;
in the presence of a base, an organic solvent optionally comprising water, and a palladium catalyst selected from the group consisting of Pd, $PdCl_2$, $Pd(OAc)_2$, $Pd(PPh_3)_4$, $PdCl_2(PPh_3)_2$, $Pd(dba)_2$, $(dppf)PdCl_2$, $Pd_2(dba)_3$, $Pd_2(dba)_3 \cdot CHCl_3$, $[PdCl(allyl)]_2$, $[PdCl_2(cod)]$, and a Pd-containing amino acid, under an inert atmosphere, to produce a compound of Formula (4):

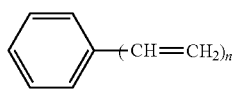
Formula (4)

wherein:
n is 2, 3, or 4; and
(ii) reacting the compound of Formula (4) above with two, three, or four compounds of Formula (5):

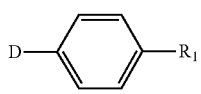
Formula (5)

wherein:
each D is independently a halogen;
each $R_1$ is independently —$(CH_2)_mC(O)OR^a$ or —$C(O)OR^a$;
each $R^a$ is independently $C_{1-4}$ alkyl; and
m is 1, 2, 3, 4, 5, 6, 7, or 8;
in the presence of a base, dry solvent, and a palladium catalyst selected from the group consisting of Pd, $PdCl_2$, $Pd(OAc)_2$, $Pd(PPh_3)_4$, $PdCl_2(PPh_3)_2$, $Pd(dba)_2$, $(dppf)PdCl_2$, $Pd_2(dba)_3$, $Pd_2(dba)_3 \cdot CHCl_3$, $[PdCl(allyl)]_2$, $[PdCl2(cod)]$, and a Pd-containing amino acid, under an inert atmosphere, to produce the compound of Formula (1) above.

2. The process of claim 1, wherein 1 equivalent of the compound of Formula (2) is reacted with 3-10 equivalents of the compound of Formula (3) in the presence of 2-10 equivalents of a base, a mixture of an organic solvent and water, 0.01-1 equivalent of dichloropalladium (II), and optionally 0.01-0.5 equivalent of a ligand, under an inert atmosphere, to form a reaction mixture.

3. The process of claim 2, wherein the process further comprises isolating or concentrating the compound of Formula (4) after step (i) and prior to step (ii).

4. The process of claim 3, wherein the isolation or concentration of the compound of Formula (4) comprises the following steps:
(a) diluting the reaction mixture with an aqueous diluent;
(b) extracting the reaction mixture with an organic solvent, to provide an organic extract containing the compound of Formula (4);
(c) washing the organic extract of step (b) above with an aqueous solvent, to provide a washed organic extract containing the compound of Formula (4);
(d) drying the washed organic extract of step (c) above, to provide a dried organic extract containing the compound of Formula (4); and
(e) concentrating the dried organic extract of step (d) above, to provide a concentrated extract containing the compound of Formula (4).

5. The process of claim 4, wherein the isolation or concentration of the compound of Formula (4) further comprises the following step:
(f) purifying the concentrated extract containing the compound of Formula (4), to provide the compound of Formula (4).

6. The process of claim 1, wherein 1 equivalent of the compound of Formula (2) is reacted with 3-10 equivalents of the compound of Formula (3) in the presence of 2-10 equivalents of cesium carbonate, a mixture of tetrahydrofuran and water, 0.01-1 equivalent of dichloropalladium (II), and 0.01-0.5 equivalent of triphenylphosphine, under an inert atmosphere, to form a reaction mixture.

7. The process of claim 1, wherein 1 equivalent of the compound of Formula (4) is reacted with 3-10 equivalents of the two, three, or four compounds of Formula (5) in the presence of 1-15 equivalents of a base, dry N,N-dimethylformamide, 0.01-1 equivalent of palladium (II) acetate or bis(dibenzylideneacetone)palladium(0) chloroform adduct, and optionally 1-10 equivalents of a ligand, under an inert atmosphere, to form a reaction mixture.

8. The process of claim 7, wherein the process further comprises isolating or concentrating the compound of Formula (1) after step (ii).

9. The process of claim 8, wherein the isolation or concentration of the compound of Formula (1) comprises the following steps:

(a) diluting the reaction mixture with an aqueous diluent;
(b) extracting the reaction mixture with an organic solvent, to provide an organic extract containing the compound of Formula (1);
(c) washing the organic extract of step (b) above with an aqueous solvent, to provide a washed organic extract containing the compound of Formula (1);
(d) drying the washed organic extract of step (c) above, to provide a dried organic extract containing the compound of Formula (1); and
(e) concentrating the dried organic extract of step (d) above, to provide a concentrated extract containing the compound of Formula (1).

10. The process of claim 9, wherein the isolation or concentration of the compound of Formula (1) further comprises the following step:

(f) purifying the concentrated extract containing the compound of Formula (1), to provide the compound of Formula (1).

11. The process of claim 1, wherein 1 equivalent of the compound of Formula (4) is reacted with 3-10 equivalents of the two, three, or four compounds of Formula (5) in the presence of 1-15 equivalents of triethylamine or potassium carbonate, dry N,N-dimethylformamide, 0.01-1 equivalent of palladium (II) acetate or bis(dibenzylideneacetone)palladium(0) chloroform adduct, and optionally tetrabutylammonium iodide, under an inert atmosphere, to form a reaction mixture.

12. The process of claim 1, wherein the process is a large-scale process.

13. The process of claim 12, wherein the large-scale process comprises at least five moles of one or more solvents or compounds selected from the group consisting of N,N-dimethylformamide, tetrahydrofuran, water, a compound of Formula (2), a compound of Formula (3), a compound of Formula (4), and a compound of Formula (5).

14. The process of claim 1, wherein n is 3.

15. The process of claim 1, wherein n is 4.

16. The process of claim 1, wherein each $R_1$ is independently —$(CH_2)_m C(O)OR^a$.

17. The process of claim 16, wherein each $R_1$ is independently —$CH_2C(O)OR^a$.

18. The process of claim 17, wherein each $R_1$ is independently selected from the group consisting of —$CH_2C(O)OCH_3$ and —$CH_2C(O)OCH_2CH_3$.

19. The process of claim 1, wherein each $R_1$ is independently —$C(O)OR^a$.

20. The process of claim 1, wherein each D is independently iodo.

21. The process of claim 1, wherein the compound of Formula (1) is selected from the group consisting of:

UNITED STATES PATENT AND TRADEMARK OFFICE
CERTIFICATE OF CORRECTION

PATENT NO.        : 10,793,495 B2                                     Page 1 of 1
APPLICATION NO.   : 15/748514
DATED             : October 6, 2020
INVENTOR(S)       : Ramiz Boulos et al.

It is certified that error appears in the above-identified patent and that said Letters Patent is hereby corrected as shown below:

On the Title Page

Item [57], Line 1, delete "a aryl" and insert -- an aryl --.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*